United States Patent [19]
Rey et al.

[11] Patent Number: 5,989,889
[45] Date of Patent: *Nov. 23, 1999

[54] NUCLEIC ACIDS ENCODING POLYPEPTIDES HAVING TRIPEPTIDE AMINOPEPTIDASE ACTIVITY

[75] Inventors: Michael Rey; Elizabeth Golightly, both of Davis, Calif.

[73] Assignee: Novo Nordisk Biotech, Inc., Davis, Calif.

[*] Notice: This patent is subject to a terminal disclaimer.

[21] Appl. No.: 08/821,118

[22] Filed: Mar. 19, 1997

Related U.S. Application Data

[63] Continuation-in-part of application No. PCT/DK95/00446, Nov. 8, 1996.

[30] Foreign Application Priority Data

Nov. 8, 1994 [DK] Denmark ................... 1288/94
Dec. 22, 1994 [DK] Denmark ................... 1470/94

[51] Int. Cl.⁶ ............... C12N 9/62; C12N 15/57; C12N 15/63; C12N 15/80
[52] U.S. Cl. ............... 435/225; 435/220; 435/69.1; 435/254.3; 435/320.1; 435/477; 435/478; 536/23.2; 536/24.32
[58] Field of Search .................. 435/225, 220, 435/69.1, 254.3, 320.1, 477, 488; 536/23.2, 24.32

[56] References Cited

U.S. PATENT DOCUMENTS 5,616,485 4/1997 Hadary et al. .................... 435/220

FOREIGN PATENT DOCUMENTS 0440303 8/1991 European Pat. Off. .
WO 92/16642 10/1992 WIPO .
WO 92/17512 6/1995 WIPO .

OTHER PUBLICATIONS

Lees, et al., *Chemical Abstracts*, vol. 113, No. 15, Abstract 128464 (Oct. 8, 1990).

Tsyperovych, et al., *Ukrainian Journal of Biochemistry* "System of Aminopeptidases from *Aspergillus flavus*", No. 1, pp. 101–105, (1977).

Krieger, et al., *FEBS Letters* vol. 352, pp. 385–388 (1994).

Balow, et al., *The Journal of Biological Chemistry*, vol. 258, No. 19, pp. 11622–11628 (Oct. 10, 1983).

Lees et al., *Biochemical Society Transactions*, vol. 18, p. 667, (1990).

Butler, et al., 1995 Applied And Environmental Microbiology, vol. 61, No. 8, pp. 3145–3150.

*Primary Examiner*—Robert A. Wax
*Assistant Examiner*—William W. Moore
*Attorney, Agent, or Firm*—Steve T. Zelson; Robert L. Starnes

[57] ABSTRACT

The present invention relates to isolated nucleic acid sequences encoding polypeptides having tripeptide aminopeptidase activity. The invention also relates; to nucleic acid constructs, vectors, and host cells comprising the nucleic acid sequences as well as recombinant methods for producing the polypeptides.

29 Claims, 5 Drawing Sheets

FIG. IA

```
ATGTTCTTCAGTCGTGGAGCGCTTTCGCTCGCAGTGCTTTCACTGCTCAGCTCCTCCGCCGCAGGGGAGG 70
  M  F  F  S  R  G  A  L  S  L  A  V  L  S  L  L  S  S  S  A  A  G  E

CTTTTGAGAAGCTGTCTGCCGTTCCAAAGGGATGGCACTATTCTAGTACCCCTAAAGGCAACACTGAGGT 140
 A  F  E  K  L  S  A  V  P  K  G  W  H  Y  S  S  T  P  K  G  N  T  E  V

TTGTCTGAAGATCGCCCTCGCGCAGAAGGATGCTGCTGGGTTCGAAAAGACCGTCTTGGAGATGTCGGAT 210
   C  L  K  I  A  L  A  Q  K  D  A  A  G  F  E  K  T  V  L  E  M  S  D

CCCGACCACCCCAGCTACGGCCAGCACTTCACCACCCACGACGAGATGAAGCGCATGCTTCTTCCCAGAG 280
  P  D  H  P  S  Y  G  Q  H  F  T  T  H  D  E  M  K  R  M  L  L  P  R

ATGACACCGTTGATGCCGTTCGACAATGGCTCGAAAACGGCGGCGTGACCGACTTTACCCAGGATGCCGA 350
 D  D  T  V  D  A  V  R  Q  W  L  E  N  G  G  V  T  D  F  T  Q  D  A  D

CTGGATCAACTTCTGTACTACCGTCGATACCGCGAACAAACTCTTGAATGCCCAGTTCAAATGGTACGTC 420
   W  I  N  F  C  T  T  V  D  T  A  N  K  L  L  N  A  Q  F  K  W  Y  V

AGCGATGTGAAGCACATCCGCCGTCTCAGAACACTGCAGTACGACGTCCCCGAGTCGGTCACCCCTCACA 490
  S  D  V  K  H  I  R  R  L  R  T  L  Q  Y  D  V  P  E  S  V  T  P  H

TCAACACCATCCAACCGACCACCCGTTTTGGCAAGATTAGCCCCAAGAAGGCCGTTACCCACAGCAAGCC 560
  I  N  T  I  Q  P  T  T  R  F  G  K  I  S  P  K  K  A  V  T  H  S  K  P

CTCCCAGTTGGACGTGACCGCCCTTGCTGCCGCTGTCGTTGCAAAGAACATCTCGCACTGTGATTCTATC 630
    S  Q  L  D  V  T  A  L  A  A  A  V  V  A  K  N  I  S  H  C  D  S  I

ATTACCCCCACCTGTCTGAAGGAGCTTTACAACATTGGTGATTACCAGGCCGATGCAAACTCGGGCAGCA 700
   I  T  P  T  C  L  K  E  L  Y  N  I  G  D  Y  Q  A  D  A  N  S  G  S

AGATCGCCTTCGCCAGCTATCTGGAGGAGTACGCGCGCTACGCTGACCTGGAGAACTTTGAGAACTACCT 770
  K  I  A  F  A  S  Y  L  E  E  Y  A  R  Y  A  D  L  E  N  F  E  N  Y  L

TGCTCCCTGGGCTAAGGGCCAGAACTTCTCCGTTACCACCTTCAACGGCGGTCTCAATGATCAGAACTCC 840
    A  P  W  A  K  G  Q  N  F  S  V  T  T  F  N  G  G  L  N  D  Q  N  S

TCGTCCGATAGCGGTGAGGCCAACCTGGACCTGCAGTACATTCTTGGTGTCAGCGCTCCACTGCCCGTTA 910
   S  S  D  S  G  E  A  N  L  D  L  Q  Y  I  L  G  V  S  A  P  L  P  V

CTGAATTCAGCACCGGAGGCCGTGGTCCCCTCGTTCCTGATCTGACCCAGCCGGATCCCAACTCTAACAG 980
  T  E  F  S  T  G  G  R  G  P  L  V  P  D  L  T  Q  P  D  P  N  S  N  S
```

FIG. IB

```
CAATGAGCCGTACCTTGAGTTCTTCCAGAATGTGTTGAAGCTCGACCAGAAGGACCTCCCCCAGGTCATC 1050
  N  E  P  Y  L  E  F  F  Q  N  V  L  K  L  D  Q  K  D  L  P  Q  V  I

TCGACCTCCTATGGAGAGAACGAACAGGAAATCCCCGAAAAGTACGCTCGCACCGTCTGCAACCTGATCG 1120
  S  T  S  Y  G  E  N  E  Q  E  I  P  E  K  Y  A  R  T  V  C  N  L  I

CTCAGCTTGGCAGCCGCGGTGTCTCCGTTCTCTTCTCCTCCGGTGACTCTGGTGTTGGCGAGGGCTGCAT 1190
  A  Q  L  G  S  R  G  V  S  V  L  F  S  S  G  D  S  G  V  G  E  G  C  M

GACCAACGACGGCACCAACCGGACTCACTTCCCACCCCAGTTCCCCGCCGCTTGCCCGTGGGTCACCTCC 1260
  T  N  D  G  T  N  R  T  H  F  P  P  Q  F  P  A  A  C  P  W  V  T  S

GTCGGCGCCACCTTCAAGACCACTCCCGAGCGCGGCACCTACTTCTCCTCGGGCGGTTTCTCCGACTACT 1330
  V  G  A  T  F  K  T  T  P  E  R  G  T  Y  F  S  S  G  G  F  S  D  Y

GGCCCCGTCCCGAATGGCAGGATGAGGCCGTGAGCAGCTACCTCGAGACGATCGGCGACACTTTCAAGGG 1400
  W  P  R  P  E  W  Q  D  E  A  V  S  S  Y  L  E  T  I  G  D  T  F  K  G

CCTCTACAACTCCTCCGGCCGTGCTTTCCCCGACGTCGCAGCCCAGGGCATGAACTTCGCCGTCTACGAC 1470
  L  Y  N  S  S  G  R  A  F  P  D  V  A  A  Q  G  M  N  F  A  V  Y  D

AAGGGCACCTTGGGCGAGTTCGACGGCACCTCCGCCTCCGCCCCGGCCTTCAGCGCCGTCATCGCTCTCC 1540
  K  G  T  L  G  E  F  D  G  T  S  A  S  A  P  A  F  S  A  V  I  A  L

TGAACGATGCCCGTCTCCGCGCCGGCAAGCCCACTCTCGGCTTCCTGAACCCCTGGTTGTACAAGACCGG 1610
  L  N  D  A  R  L  R  A  G  K  P  T  L  G  F  L  N  P  W  L  Y  K  T  G

CCGCCAGGGTCTGCAAGATATCACCCTCGGTGCTAGCATTGGCTGCACCGGTCGCGCTCGCTTCGGCGGC 1680
  R  Q  G  L  Q  D  I  T  L  G  A  S  I  G  C  T  G  R  A  R  F  G  G

GCCCCTGACGGTGGTCCCGTCGTGCCTTACGCTAGCTGGAACGCTACCCAGGGCTGGGATCCCGTCACTG 1750
  A  P  D  G  G  P  V  V  P  Y  A  S  W  N  A  T  Q  G  W  D  P  V  T

GTCTCGGAACTCCCGATTTCGCCGAGCTCAAGAAGCTTGCCCTTGGCAACTAA 1803
  G  L  G  T  P  D  F  A  E  L  K  K  L  A  L  G  N
```

FIG. 2

```
A. niger    1    M L S S L L S Q G A A V S L A V L S L L P S P V A A E I F E K L S G V P
A. oryzae   1    - - - M F F S R G - A L S L A V L S L L S S S A A G E A F E K L S A V P A. niger    37   N G W R Y A N N P Q G N E V I R L Q I A L Q Q H D V A G F E Q A V M D M
A. oryzae   33   K G W H Y S S T P K G N T E V C L K I A L A Q K D A A G F E K T V L E M A. niger    73   S T P G H A D Y G K H F R T H D E M K R M L L P S E T A V D S V R D W L
A. oryzae   69   S D P D H P S Y G Q H F T T H D E M K R M L L P R D D T V D A V R Q W L A. niger    109  E S A G V H N I Q V D A D W V K F H T T V N K A N A L L D A D F K W Y V
A. oryzae   105  E N G G V T D F T Q D A D W I N F C T T V D T A N K L L N A Q F K W Y V A. niger    145  S D A K H I R R L R T L Q Y S I P D A L V S H I N M I Q P T T R F G Q I
A. oryzae   141  S D V K H I R R L R T L Q Y D V P E S V T P H I N T I Q P T T R F G K I A. niger    181  Q P N R A T M R S K P K H A D E T F L T A A T L A Q N T S H C D S I I T
A. oryzae   177  S P K K A V T H S K P S Q L D V T A L A A A V V A K N I S H C D S I I T A. niger    217  P H C L K Q L Y N I G D Y Q A D P K S G S K I G F A S Y L E E Y A R Y A
A. oryzae   213  P T C L K E L Y N I G D Y Q A D A N S G S K I A F A S Y L E E Y A R Y A A. niger    253  D L E R F E Q H L A P N A I G Q N F S V Q F N G G L N D Q L S S S D S
A. oryzae   249  D L E N F E N Y L A P M A K G Q N F S V T T F N G G L N D Q N S S S D S A. niger    289  G E A N L D L Q Y I L G V S A P V P I T E Y S T G G R G E L V P D L S S
A. oryzae   285  G E A N L D L Q Y I L G V S A P L P V T E F S T G G R G P L V P D L T Q A. niger    325  P D P N D N S N E P Y L D F L Q G I L K L N N S D L P Q V I S T S Y G E
A. oryzae   321  P D P N S N S N E P Y L E F F Q N V L K L D Q K D L P Q V I S T S Y G E A. niger    361  D E Q T I P V P Y A R T V C N L Y A Q L G S R G V S V I F S S G D S G V
A. oryzae   357  N E Q E I P E K Y A R T V C N L I A Q L G S R G V S V L F S S G D S G V A. niger    397  G A A C L T N D G T N R T H F P P Q F P A S C P W V T S V G A T S K T S
A. oryzae   393  G E G C M T N D G T N R T H F P P Q F P A A C P W V T S V G A T F K T T A. niger    433  P E Q A V S F S S G G F S D L W P R P S Y Q H A A V Q T Y L T K H L G N
A. oryzae   429  P E R G T Y F S S G G F S D Y W P R P E W Q D E A V S S Y L E T - I G D A. niger    469  K F S G L F N A S G R A F P D V S A Q G V N Y A V Y D K G M L G Q F D G
A. oryzae   464  T F K G L Y N S S G R A F P D V A A Q G M N F A V Y D K G T L G E F D G A. niger    505  T S C S A P T F S G V I A L L N D A R L R A G L P V M G F L N P F L Y G
A. oryzae   500  T S A S A P A F S A V I A L L N D A R L R A G K P T L G F L N P M L Y K A. niger    541  V G S E K G A L N D I V N G G S V G C D G R N R F G G T P N G S P V V P
A. oryzae   536  T G R Q - - G L Q D I T L G A S I G C T G R A R F G G A P D G G P V V P A. niger    577  F A S W N A T T G W D P V S G L G T P D F A K L K G V A L G E E G G N
A. oryzae   570  Y A S W N A T Q G W D P V T G L G T P D F A E L K K L A L G N - - - -
```

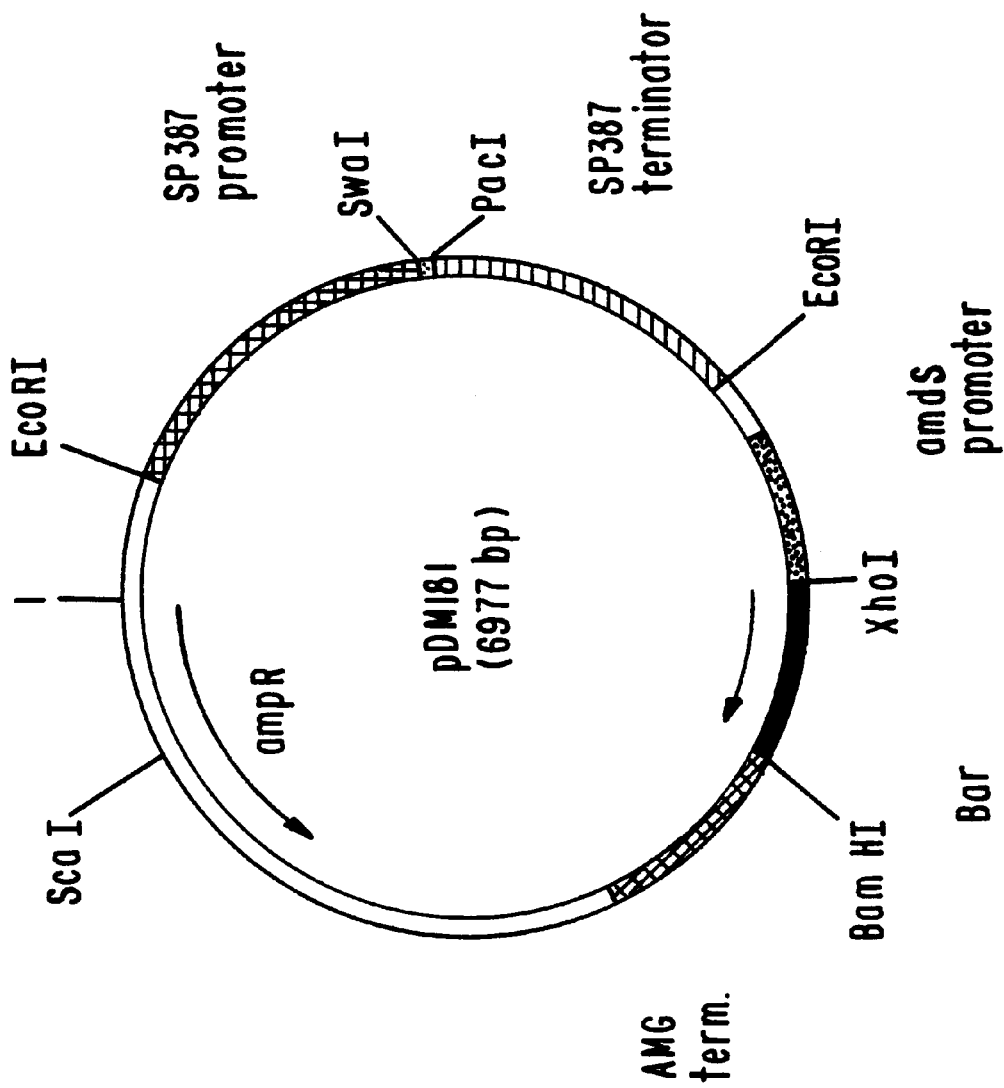

/ 1

NUCLEIC ACIDS ENCODING POLYPEPTIDES HAVING TRIPEPTIDE AMINOPEPTIDASE ACTIVITY

CROSS-REFERENCE TO RELATED APPLICATIONS

This application is a continuation-in-part of PCT/DK95/00446 filed Nov. 8, 1996, which claims priority of Danish application serial nos. 1288/94 filed Nov. 8, 1994 and 1470/94 filed Dec. 22, 1994, the contents of which applications are fully incorporated herein by reference.

BACKGROUND OF THE INVENTION

1. Field of the Invention

The present invention relates to isolated nucleic acid sequences encoding polypeptides having tripeptide aminopeptidase activity. The invention also relates to nucleic acid constructs, vectors, and host cells comprising the nucleic acid sequences as well as recombinant methods for producing the polypeptides.

2. Description of the Related Art

Tripeptide aminopeptidases (EC 3.4.11.4) are exopeptidases which catalyze the removal of unsubstituted tripeptides from the N-terminus of peptides, oligopeptides or proteins. Tripeptide aminopeptidases may be unspecific in cleaving any tripeptide sequence from the N-terminal end, or specific in cleaving specific types of tripeptide sequences.

The isolation of microbial genes encoding tripeptide aminopeptidases have been reported previously. For instance, Butler et al. disclose the cloning and expression of a *Streptomyces lividans* tripeptide aminopeptidase gene (1995, *Applied and Environmental Microbiology* 61:3145–3150). Mierau et al. disclose the cloning and expression of a *Lactococcus lactis* tripeptide aminopeptidase gene (1994, *Journal of Bacteriology* 176: 2854–2861).

It is an object of the present invention to provide isolated nucleic acid sequences encoding polypeptides have tripeptide aminopeptidase activity.

SUMMARY OF THE INVENTION

The present invention relates to isolated nucleic acid sequences encoding polypeptides having tripeptide aminopeptidase activity selected from the group consisting of:

(a) a nucleic acid sequence which is capable of hybridizing under high stringency conditions with (i) the nucleic acid sequence set forth in SEQ ID NO:1 or (ii) its complementary strand;

(b) a nucleic acid sequence encoding a polypeptide having tripeptide aminopeptidase activity with an amino acid sequence which has at least 75% identity with the amino acid sequence set forth in SEQ ID NO:2;

(c) an allelic form of (a) or (b); and (d) a fragment of (a), (b), or (c).

The present invention also relates to nucleic acid constructs, vectors, and host cells comprising the nucleic acid sequences as well as recombinant methods for producing the polypeptides.

BRIEF DESCRIPTION OF THE FIGURES

FIG. 1 shows the nucleic acid sequence and the deduced amino acid sequence of the *Aspergillus oryzae* ATCC 20386 tripeptide aminopeptidase I (SEQ ID NOS:1 and 2).

FIG. 2 shows a sequence comparison of the *Aspergillus oiyzae* ATCC 20386 tripeptide aminopeptidase I and *Aspergillus niger* tripeptide aminopeptidase (SEQ ID NO:5).

FIG. 3 shows a restriction map of pDM181.

DETAILED DESCRIPTION OF THE INVENTION

Nucleic Acid Sequences

Figure 4:
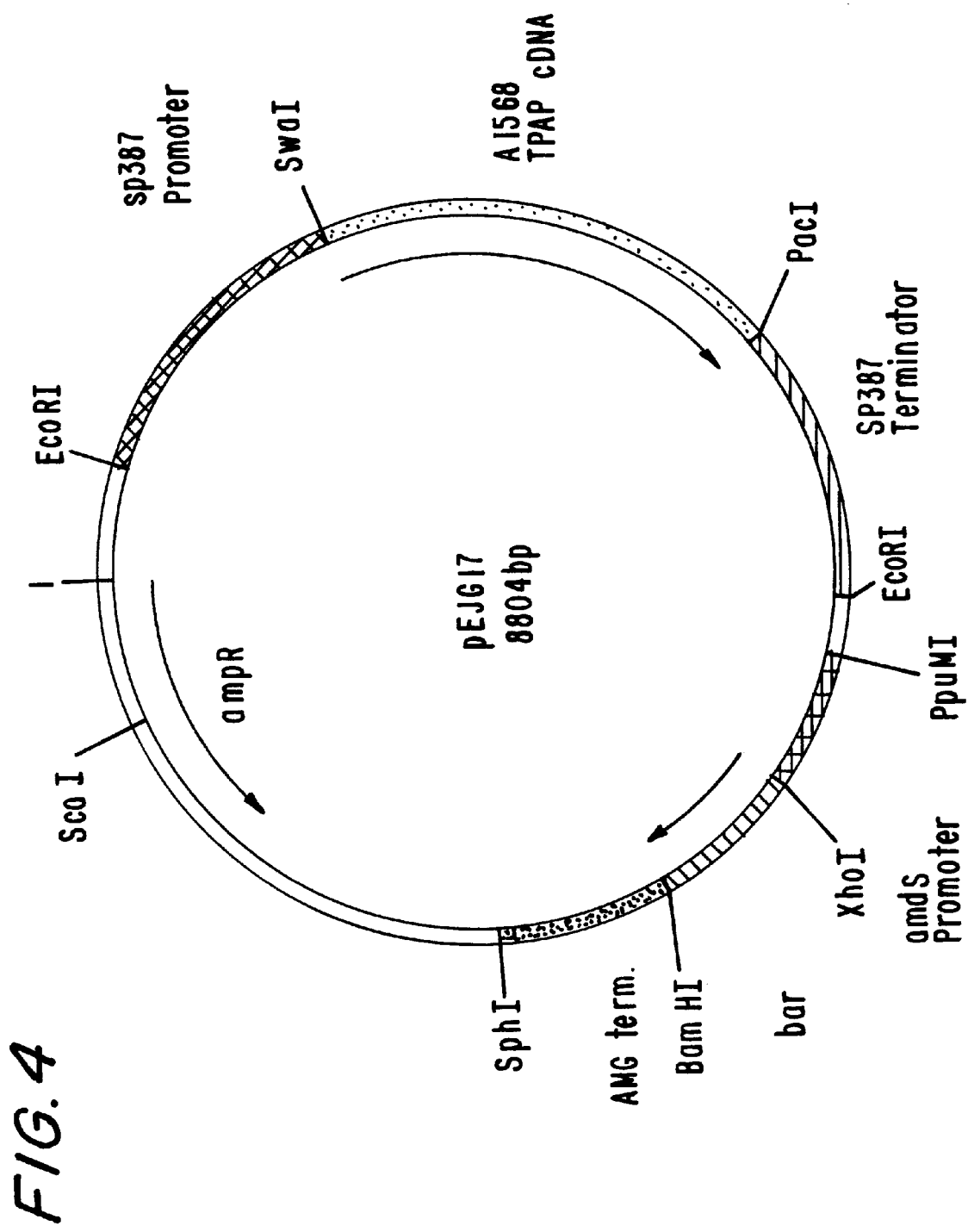
FIG. 4 shows a restriction map of pEJG17.

The term "tripeptide aminopeptidase" is defined herein as an aininopeptidase which cleaves tripeptides from the N-terminal end of a peptide, polypeptide, or protein sequence. Defined in a general manner, the tripeptide aminopeptidase is capable of cleaving the tripeptide XYZ from the unsubstituted N-terminal amino group of a peptide, polypeptide, or protein, wherein X, Y, or Z represents any amino acid residue selected from the group consisting of Ala, Arg, Asn, Asp, Cys, Gln, Glu, Gly, His, Ile, Leu, Lys, Met, Phe, Pro, Ser, Thr, Trp, Tyr, and Val. All of X, Y, and Z may be different or identical or two of X, Y, and Z may be identical. It will be understood that the tripeptide aminopeptidases encoded by the isolated nucleic acid sequences of the present invention are unspecific as to the amino acid sequence of the tripeptide to be cleaved.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined, for example, by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, or synthetic origin, or any combinations thereof.

In a first embodiment, the present invention relates to isolated nucleic acid sequences encoding polypeptides with tripeptide aminopeptidase activity which are capable of hybridizing under high, medium, or low stringency conditions with an oligonucleotide probe which hybridizes under the same conditions with the nucleic acid sequence set forth in SEQ ID NO:1 or its complementary strand (J. Sambrook, E. F. Fritsch, and T. Maniatis, 1989, *Molecular Cloning, A Laboratory Manual*, 2d edition, Cold Spring Harbor, N.Y.), and allelic forms and fragments thereof. Hybridization indicates that the analogous nucleic acid sequence hybridizes to the oligonucleotide probe corresponding to the polypeptide encoding part of the nucleic acid sequence shown in SEQ ID NO:1, under low to high stringency conditions (for example, prehybridization and hybridization at 42° C. in 5× SSPE, 0.3% SDS, 200 μg/ml sheared and denatured salmon sperm DNA, and either 50, 35 or 25% formamide for high, medium and low stringencies, respectively), following standard Southern blotting procedures. In a preferred embodiment, the nucleic acid sequences are capable of hybridizing under high stringency conditions with the nucleic acid sequence set forth in SEQ ID NO:1, its complementary strand, or a subsequence thereof.

SEQ ID NO:1 as well as SEQ ID NO:2, or subsequences thereof, may be used to design an oligonucleotide probe to isolate homologous genes encoding tripeptide aminopeptidases from other strains of different genera or species according to methods well known in the art. Thus, a genomic or cDNA library prepared from such other organisms may be screened for DNA which hybridizes with such probes following standard Southern plotting procedures, in order to identify and isolate the corresponding gene therein. Such probes can be considerably shorter than the entire sequence, but should be at least 15, preferably at least 25, and more preferably at least 40 nucleotides in length. Longer probes, preferably no more than 1200 nucleotides in length, can also be used. Both DNA and RNA probes can be used. The probes are typically labeled for detecting the corresponding gene (for example, with $^{32}$P, $^{3}$H, biotin, or avidin). A PCR reaction using the degenerate probes mentioned herein and genomic DNA or first-strand cDNA from an Aspergilus strain can also yield an Aspergillus tripeptide aminopeptidase-specific product which can then be used as a probe to clone the corresponding genomic or cDNA.

Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify clones or DNA which are homologous with SEQ ID NO:1, the carrier material is used in a Southern blot in which the carrier material is finally washed three times for 30 minutes each using 2× SSC, 0.2% SDS at preferably not higher than 40° C., more preferably not higher than 45° C., more preferably not higher than 50° C., more preferably not higher than 55° C., even more preferably not higher than 60° C., especially not higher than 65° C. Molecules to which the oligonucleotide probe hybridizes under these conditions are detected using X-ray film.

In a second embodiment, the present invention relates to isolated nucleic acid sequences encoding polypeptides with tripeptide aminopeptidase activity which have an amino acid sequence with a degree of identity to the amino acid sequence set forth in SEQ ID NO:2 of at least about 75%, preferably about 80%, more preferably about 85%, even more preferably about 90%, most preferably about 95%, and even most preferably about 97%, which qualitatively retain the activity of the polypeptides (hereinafter "homologous polypeptides"), and allelic forms and fragments thereof. In a preferred embodiment, the homologous polypeptides have an amino acid sequence which differs by five amino acids, preferably by four amino acids, more preferably by three amino acids, even more preferably by two amino acids, and most preferably by one amino acid from the amino acid sequence set forth in SEQ ID NO:2. For purposes of the present invention, the degree of identity between two amino acid sequences or between nucleic acid sequences is determined by the Clustal method with an identity table, a gap penalty of 10, and a gap length penalty of 10 (Higgins, 1989, *CABIOS* 5: 151–153).

In a preferred embodiment, the present invention relates to isolated nucleic acid sequences which encode polypeptides having tripeptide aminopeptidase activity with an amino acid sequence set forth in SEQ ID NO:2, and allelic forms and fragments thereof. In a specific embodiment, the nucleic acid sequence is set forth in SEQ ID NO:1, and allelic forms and fragments thereof. The nucleic acid sequences of the present invention also encompass nucleic acid sequences which encode a polypeptide having the amino acid sequence set forth in SEQ ID NO:2, but differ from SEQ ID NO:1 by virtue of the degeneracy of the genetic code. In a preferred embodiment, the nucleic acid sequence of the present invention is the nucleic acid sequence contained in plasmid pEJG12 which is contained in *Escherichia coli* NRRL B-21616. The present invention also relates to subsequences of SEQ ID NO:1 which encode a fragment of SEQ ID NO:2 and retain tripeptide aminopeptidase activity.

The amino acid sequences of the homologous polypeptides encoded by the nucleic acid sequences of the present invention may differ from the amino acid sequence set forth is in SEQ ID NO:2 by an insertion or deletion of one or more amino acid residues and/or the substitution of one or more amino acid residues by different amino acid residues. Preferably, amino acid changes are of a minor nature, that is conservative amino acid substitutions which do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine and valine), aromatic amino acids (such as phenylalanine, tryptophan and tyrosine), and small amino acids (such as glycine, alanine, serine, threonine and methionine). Amino acid substitutions which do not generally alter the specific activity are known in the art and are described, e.g., by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

The isolated nucleic acid sequences of the present invention which are capable of hybridizing with an oligonucleotide probe which hybridizes with the nucleic acid sequence set forth in SEQ ID NO:1, its complementary strand, or a subsequence thereof, may be obtained from microorganisms of any genus, for example, from a bacterial or fungal source, but preferably from a fungal cell, and more preferably from a filamentous fungal cell or a yeast cell. For purposes of the present invention, the term "obtained from" (or endogenous to) as used herein in connection with a given source shall mean that the polypeptide is produced by the source or by a cell in which a gene from the source has been inserted. Preferred sources for homologous genes are strains of the genus Aspeigillus and species thereof available in public depositories. Furthermore, homologous genes may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Particularly preferred strains are filamentous fungus strains, such as an Acremonium, Aspergillus, Aureobasidium, Cryptococcus, Filibasidium, Ftsarium, Humicola, Magnaporthe, Mucor, Myceliophthora, Neocallimastix, Neurospcra, Paecilomyces, Penicillium, Piromyces, Schizophyllum, Talaromyces, Thermoascus, Thielavia, Tolypocladium, or Trichoderma strain or yeast strains, such as a Candida, Kluyveromyces, Pichia, Saccharomyces, Schizosaccharomyces, or Yarrowia strain.

In a preferred embodiment, a nucleic acid sequence of the present invention is obtained from a strain of the genus Aspergillus, as defined by Raper, K. D. and Fennel, D. I., 1965, *The Genus Aspergillus*, The Wilkins Company, Baltimore, such as a strain of *Aspergillus aculeatus, Aspergillus awamori, Aspergillus foetidus, Aspergillus japonicus, Aspergillus nidulans, Aspergillus niger*, or *Aspergillus oryzae* strain. In an even more preferred embodiment, the nucleic acid sequence is obtained from *Aspergillus oryzae* and in a most preferred embodiment, the nucleic acid sequence is obtained from *Aspergillus oryzae* ATCC 20386, e.g., the nucleic acid sequence set forth in SEQ ID NO:1. In another preferred embodiment, the nucleic acid sequence is obtained from a Trichoderma strain, such as a strain of *Trichoderma harzianum, Trichoderma koningii, Trichoderma longibrachiatum, Trichoderma reesei*, or *Trichoderma viride*. In another preferred embodiment, the nucleic acid sequence is obtained from a Fusarium strain, such as a strain of *Fusarium cerealis, Fusarium crookwellense, Fusarium graminearum, Fusarium oxyspisrum, Fusarium sulphureum, Fusarium sambucinum*, or *Fusarium venenatum*.

The isolated nucleic acid sequences of the present invention may also be obtained from microorganisms which are synonyms or teleomorphs of Aspergillus as defined by Raper, K. D. and Fennel, D. I., 1965, supra. Aspergilli are mitosporic fungi characterized by an aspergillum comprised of a conidiospore stipe terminating in a vesicle, which in turn bears one or two layers of synchronously formed specialized cells, variously referred to as sterigmata or phialides, and asexually formed spores referred to as conidia. Known teleomorphs of Aspergillus include Emericella, Eurotium, and Neosattorya. Strains of Aspergillus and teleomorphs thereof are readily accessible to the public in a number of culture collections, such as the American Type Culture Collection (ATCC), Deutsche Sammlung von Mikroorganismen und Zellkulturen GmbH (DSM), Contraalbureau Voor Schimmelcultures (CBS), and Agricultural Research Service Patent Culture Collection, Northern Regional Research Center (NRRL).

Once a nucleic acid sequence has been detected with the probe(s) described above, the sequence may be isolated or cloned by utilizing techniques which are well known to those of ordinary skill in the art (see, e.g., Sambrook et al., 1989, supra). The known techniques used to isolate or clone a nucleic acid sequence include isolation from genomic DNA, preparation from cDNA, or a combination thereof. The cloning of the nucleic sequences of the present invention from such genomic DNA can be effected, e.g., by using the well known polymerase chain reaction (PCR). See, for example, Innis et al., 1990, *PCR Protocols: A Guide to Methods and Application*, Academic Press, New York. The nucleic acid sequence may be cloned from a strain of Aspergillus producing the polypeptide, or another or related organism and thus, for example, may be an allelic or species variant of the polypeptide encoding region of the nucleic acid sequence.

Modification of the nucleic acid sequence encoding the polypeptide may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source. For example, it may be of interest to synthesize variants of the polypeptide where the variants differ in specific activity, thermostability, oxidative stability, pH optimum, or the like using, for example, site-directed mutagenesis. The analogous sequence may be constructed on the basis of the nucleic acid sequence presented as the polypeptide encoding region of SEQ ID NO:1, a sub-sequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Frotein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique mutations are introduced at every positively charged residue in the molecule, and the resultant mutant molecules are tested for tripeptide aminopeptidase activity to identify amino acid residues that are critical to the activity of the molecule. Sites of substrate-enzyme interaction can also be determined by analysis of crystal structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

Polypeptides encoded by the nucleic acid sequences of the present invention also include fused polypeptides in which another polypeptide is fused at the N-terminus or the C-terminus of the polypeptide or fragment thereof. A fused polypeltide is produced by fusing a nucleic acid sequence (or a portion thereof) encoding another polypeptide to a nucleic acid sequence (or a portion thereof) of the present invention. Techniques for producing fusion polypeptides are known in the art, and include, ligating the coding sequences encoding the polypeptides so that they are in frame and that expression of the fused polypeptide is under control of the same promoter(s) and terminator.

Nucleic Acid Constructs

The present invention also relates to nucleic acid constructs comprising a nucleic acid sequence of the present invention operably linked to one or more control sequences capable of directing the expression of the coding sequence in a suitable host cell under conditions compatible with the control sequences. "Nucleic acid construct" is defined herein as a nucleic acid molecule, either single-or double-stranded, which is isolated from a naturally occurring gene or which has been modified to contain segments of nucleic acid which are combined and juxtaposed in a manner which would not otherwise exist in nature. The term nucleic acid construct may be synonymous with the term expression cassette when the nucleic acid construct contains all the control sequences required for expression of a coding sequence of the present invention. The term "coding sequence" as defined herein is a sequence which is transcribed into MRNA and translated into a polypeptide of the present invention when placed under the control of the appropriate control sequences. The boundaries of the coding sequence are generally determined by a translation start codon ATG at the 5'-terminus and a translation stop codon at the 3'-terminus. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence encoding a polypeptide prior to its insertion into a vector may be desirable or necessary depending on the expression vector. The techniques for modifying nucleic acid sequences utilizing cloning methods are well known in the art.

The term "control sequences" is defined herein to include all components which are necessary or advantageous for expression of the coding sequence of the nucleic acid sequence. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothemophilus* maltogenic amylase gene (amyM), the *Bacillus amyloliquefaciens* alpha-amylase gene (amyQ), the *Bacillus lichenifomis* penicillinase gene (penP), the *Bacillus subtilis* xylA and xylB genes, and the prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242:74–94; and in Sambrook et al., 1989, supra.

Examples of suitable promoters for directing the transcription of the nucleic acid constructs of the present invention in a filamentous fungal host cell are promoters obtained from the genes encoding Aspergillus oryzae TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (as described in U.S. Pat. No. 4,288,627, which is incorporated herein by reference), and hybrids, mutants or truncated promoters thereof. Particularly preferred promoters for use in filamentous fungal host cells are the TAKA amylase, NA2-tpi (a hybrid of the promoters from the genes encoding *Aspergillus niger* neutral a-amylase and *Aspergillus oryzae* triose phosphate isomerase), and glaa promoters.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8: 423–488. In a mammalian host cell, useful promoters include viral promoters such as those from Simian Virus 40 (SV40), Rous sarcoma virus (RSV), adenovirus, and bovine papilloma virus (BPV).

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes encoding *Aspergillus oryzae* TAKA amylase, *Aspergillus niger* glucoarrmylase, *Aspergillus nidulans* anthranilate synthase, *Aspergillus niger* alpha-glucosidase, and *Fusarium oxysporum* trypsin-like protease.

Preferred terminators for yeast host cells are obtained from the genes encoding *Saccharomyces cerevisiae* enolase, *Saccharomyces cerevisiae* cytochrorme C (CYC1), or *Saccharomyces cerevisiae* glyceraldehyde-3-phosphate dehydrogenase. Other useful terminators for yeast host cells are described by Romanos et al., 1992, supra. Terminator sequences are well known in the art for mammalian host cells.

The control sequence may also be a suitable leader sequence, a nontranslated region of a mRNA which is important for translation by the host cell. The leader sequence is operably linked to the 5' terminus of the nucleic acid sequence encoding the polypeptide. Any leader sequence which is functional in the host cell of choice may be used in the present invention.

Preferred leaders for filamentous fungal host cells are obtained from the genes encoding *Aspergillus oryzae* TAKA amylase and *Aspergillus oryzae* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes encoding *Aspergillus oryzae* TAKA amylase, *Aspergilluis niger* glucoamylase, *Aspergillus nidulans* anthranilate synthase, and *Aspergillus niger* alpha-amylase.

Useful polyadenylation sequences for yeast host cells are described by Guo and Sherman, 1995, *Molecular Cellular Biology* 15: 5983–5990. Polyadenylation sequences are well known in the art for mammalian host cells.

The control sequence may also be a signal peptide coding region, which codes for an amino acid sequence linked to the amino terminus of the polypeptide which can direct the expressed polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to that portion of the coding sequence which encodes the secreted polypeptide. The foreign signal peptide coding region may be required where the coding sequence does not normally contain a signal peptide coding region. Alternatively, the foreign signal peptide coding region may simply replace the natural signal peptide coding region in order to obtain enhanced secretion of the tripeptide aminopeptidase relative to the natural signal peptide coding region normally associated with the coding sequence. The signal peptide coding region may be obtained from a glucoamylase or an amylase gene from an Aspergillus species, a lipase or proteinase gene from a Rhizomucor species, the gene for the alpha-factor from *Saccharomyces cerevisiae*, an amylase or a prdtease gene from a Bacillus species, or the calf preprochymosin gene. However, any signal peptide coding region capable of directing the expressed tripeptide aminopeptidase into the secretory pathway of a host cell of choice may be used in the present invention.

An effective signal peptide coding region for bacterial host cells is the signal peptide coding region obtained from the maltogenic amylase gene from Bacilius NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* prsA gene. Further signal peptides are described by Simonen and Palva, 1993, *Microbiological Reviews* 57: 109–137.

An effective signal peptide coding region for filamentous fungal host cells is the signal peptide coding region obtained from *Aspergillus oryzae* TAKA amylase gene, *Aspergillus niger* neutral amylase gene, the *Rhizomucor miehei* aspartic proteinase gene, the *Humicola lanuginosa* cellulase gene, or the *Rhizomucor miehei* lipase gene.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, or the *Myceliophthora thermophilum* laccase gene (WO 95/33836).

The nucleic acid constructs of the present invention may also comprise one or more nucleic acid sequences which encode one or more factors that are advantageous in the expression of the polypeptide, e.g., an activator (e.g., a trans-acting factor), a chaperone, and a processing protease. Any factor that is functional in the host cell of choice may be used in the present invention. The nucleic acids encoding one or more of these factors are not necessarily in tandem with the nucleic acid sequence encoding the polypeptide.

An activator is a protein which activates transcription of a nucleic acid sequence encoding a polypeptide (Kudla et al., 1990, *EMBO Journal* 9: 1355–1364; Jarai and Buxton, 1994, *Current Genetics* 26: 2238–244; Verdier, 1990, *Yeast* 6: 271–297). The nucleic acid sequence encoding an activator may be obtained from the genes encoding *Bacillus stearothemophilus* NprA (nprA), *Saccharomyces cerevisiae* heme activator protein 1 (hap1), *Saccharomyces cerevisiae* galactose metabolizing protein 4 (gal4), and *Aspergillus nidulans* ammonia regulation protein (areA). For further examples, see Verdier, 1990, supra and MacKenzie et al., 1993, *Journal of General Microbiology* 139: 2295–2307.

A chaperone is a protein which assists another polypeptide in folding properly (Hartl et al., 1994, *TIBS* 19: 20–25; Bergeron et al., 1994, *TIBS* 19: 124–128; Demolder et al., 1994, *Journal of Biotechnology* 32: 179–189; Craig, 1993, *Science* 260: 1902–1903; Gething and Sambrook, 1992, *Nature* 355: 33–45; Puig and Gilbert, 1994, *Journal of Biological Chemistry* 269: 7764–7771; Wang and Tsou, 1993, *The FASEB Journal* 7: 1515–11157; Robinson et al., 1994, *Bio/Technology* 1: 381–384). The nucleic acid sequence encoding a chaperone may be obtained from the genes encoding *Bacillus subtilis* GroE proteins, *Aspergillus oryzae* protein disulphide isomerase, *Saccharomyces cerevisiae* calnexin, *Saccharomyces cerevisiae* BiP/GRP78, and *Saccharomyces cerevisiae* Hsp70. For further examples, see Gething and Sambrook, 1992, supra, and Hartl et al., 1994, supra.

A processing protease is a protease that cleaves a propeptide to generate a mature biochemically active polypeptide (Enderlin and Ogrydziak, 1994, *Yeast* 10: 67–79; Fuller et al., 1989, *Proceedings of the National Academy of Sciences USA* 86: 1434–1438; Julius et al., 1984, *Cell* 37: 1075–1089; Julius et al., 1983, *Cell* 32: 839–852). The nucleic acid sequence encoding a processing protease may be obtained from the genes *Saccharomyces cerevisiae* dipeptidylaminopeptidase, *Saccharomyces cerevisiae* Kex2, and *Yarrowia lipolytica* dibasic processing endoprotease (xpr6).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention may be integrated into the host cell genome when introduced into a host cell. For integration, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination. These nucleic acid sequences may be any sequence that is homologous with a target sequence in the genome of the host cell, and, furthermore, may be non-encoding or encoding sequences.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in Bacillus. Examples of origin of replications for use in a yeast host cell are the 2 micron origin of replication, ARS1, ARS4, the combination of CEN6 and ARS4, and the combination of CEN3 and ARS1. The origin of replication may be one having a mutation which makes its functioning temperature-sensitive in the host cell (see, e.g., Ehrlich, 1978, *Proceedings of the National Academy of Sciences USA* 75: 1433). In a specific embodiment, the expression vector may be plasmid pEJG13.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. A frequently used mammalian marker is the dihydrofolate reductase gene. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), and glufosinate resistance markers, as well as equivalents from other species. Preferred for use in an Aspergillus cell are the amdS and pyrG genes of *Aspergillus nidulans* or *Aspergillus oryzae* and the bar gene of *Streptomyrces hygroscopicus*. Furthermore, selection may be accomplished by co-transformation, e.g., as described in WO 91/17243, where the selectable marker is on a separate vector.

More than one copy of a nucleic acid sequence encoding a polypeptide of the present invention may be inserted into the host cell to amplify expression of the nucleic acid sequence. Stable amplification of the nucleic acid sequence can be obtained by integrating at least one additional copy of the sequence into the host cell genome using methods well known in the art and selecting for transformants.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. The term "host cell" encompasses any progeny of a. parent cell which is not identical to the parent cell due to mutations that occur during replication.

The cell is preferably transformed with a vector comprising a nucleic acid sequence of the invention followed by integration of the vector into the host chromosome. "Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome occurs homologous or non-homologous recombination as described above.

The choice of a host cell will to a large extent depend upon the gene encoding the polypeptide and its source. The host cell may be a unicellular microorganism, e.g., a prokaryote, or a non-unicellular microorganism, e.g., a eukaryote. Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus coagulans, Bacillus firmus, Bacillus lautus, Bacillus lentus, Bacillus lichenifomis, Bacillus megaterium, Bacillus pumilus, Bacillus stearothermophilus, Bacillus subtilis,* and *Bacillus thuringiensis*; or a Streptomyces cell, e.g., *Streptomycesliviiians* or *Streptomyces murinus*, or gram negative bacteria such as *E. coli* and Pseudomonas sp. In a preferred embodiment, the bacterial host cell is a *Bacillus lentus, Bacillus lichenifomis, Bacillus stearothermophilus* or *Bacillus subtilis* cell. The transformation of a bacterial host cell may, for instance, be effected by protoplast transformation (see, e.g., Chang and Cohen, 1979, *Molecular General Genetics* 168: 111–115), by using competent cells (see, e.g., Young and Spizizin, 1961, *Journal of Bacteriology* 81: 823–829, or Dubnau and Davidoff-Abelson, 1971, *Journal of Molecular Biology* 56: 209–221), by electroporation (see, e.g., Shigekawa and Dower, 1988, *Biotechniques* 6: 742–751), or by conjugation (see, e.g., Koehler and Thorne, 1987, *Journal of Bacteriology* 169: 5771–5278).

The host cell may be a eukaryote, such as a mammalian cell, in insect cell, a plant cell or a fungal cell. Useful mammalian cells include Chinese hamster ovary (CHO) cells, HeLa cells, baby hamster kidney (BHK) cells, COS cells, or any number of other immortalized cell lines available, e.g., from the American Type Culture Collection.

In a preferred embodiment, the host cell is a fungal cell. "Fungi" as used herein includes the phyla Ascomycota, Basidiomycota, Chytridiomycota, arid Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). Representative groups of Ascomycota include, e.g., Neurospora, Eupenicillium (=Penicillium), Emericella (=Aspergillus), Eurotium (=Aspergillus), and the true yeasts listed below. Examples of Basidiomycota include mushrooms, rusts, and smuts. Representative groups of Chytridiomycota include, e.g., Allomyces, Blastocladiella, Coelomomyces, and aquatic fungi. Representative groups of Oomycota include, e.g., Saprolegniomycetous aquatic fungi (water molds) such as Achlya. Examples of mitosporic fungi include Aspergillus, Penicillium, Candida, and Alternaria. Representative groups of Zygomycota include, e.g., Rhizopus and Mucor.

In a preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e. g., genus Schizosaccharomyces), Nadsonioideae, Lipomycoideae, and Saccharomycoideae (e.g., genera Pichia, Kluyveromyces and Saccharomyces). The basidiosporogenous yeasts include the genera Leucosporidim, Rhodosporidium, Sporidiobolus, Filobasidium, and Filobasidiella. Yeast belonging to the Fungi Imperfecti are divided into two families, Sporobolomycetaceae (e.g., genera Sorobolomyces and Bullera) and Cryptococcaceae (e.g., genus Cidndida). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., *Biochemistry and Genetics of Yeast*, Bacil, M., Horecker, B. J., and Stopani, A. O. M., editors, 2nd edition, 1987; *The Yeasts*, Rose, A. H., and Harrison, J. S., editors, 2nd edition, 1987; and *The Molecular Biology of the Yeast Saccharomyces*, Strathem et al., editors, 1981).

In a more preferred embodiment, the yeast host cell is a cell of a species of Candida, Kluyveromyces, Saccharomyces, Schizosaccharomyces, Pichia, or Yarnowia.

In a most preferred embodiment, the yeast host cell is, a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In a preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a vegetative mycelial wall composed of chitin, cellulose, glucan, chitosan, mannan, and other complex polysaccharides. Vegetative growth is by typhal elongation and carbon catabolism is obligately aerobic. In contrast, vegetative growth by yeasts such as *Saccharomyces cerevisiae* is by budding of a unicellular thallus and carbon catabolism may be fermentative. In a more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, and Trichoderma.

In an even more preferred embodiment, the filamentous fungal host cell is an Aspergillus cell. In another even more preferred embodiment, the filamentous fungal host cell is an Acremonium cell. In another even more preferred embodiment, the filamentous fungal host cell is a Fusarium cell. In another even more preferred embodiment, the filamentous fungal host cell is a Humicola cell. In another even more preferred embodiment, the filamentous fungal host cell is a Mucor cell. In another even more preferred embodiment, the filamentous fungal host cell is a Myceliophthora cell. In another even more preferred embodiment, the filamentous fungal host cell is a Neurospora cell. In another even more preferred embodiment, the filamentous fungal host cell is a Penicillium cell. In another even more preferred embodiment, the filamentous fungal host cell is a Thielavia cell. In another even more preferred embodiment, the filamentous fungal host cell is a Tolypocladium cell. In another even more preferred embodiment, the filamentous fungal host cell is a Trichoderma cell.

In a most preferred embodiment, the filamentous fungal host cell is an *Aspergillus awamori, Aspergillusfoetidus, Aspergillus japonicus, Aspergillus nidulans, Aspergillus niger* or *Aspergillus oryzae* cell. In another most preferred embodiment, the filamentous fungal host cell is a *Fusarium cerealis, Fusarium crookwellense, Fusarium gramninearum, Fusarium oxysporum, Fusarium sambucinum, Fusarium sulphureum,* or *Fusariumir venenatum* cell. In another most preferred embodiment, the filamentous fungal host cell is a *Humicola insolens* or *Humicola lanuginosa* cell. In another most preferred embodiment, the filamentous fungal host cell is a *Mucor miehei* cell. In another most preferred embodiment, the filamentous fungal host cell is a *Myceliophthora thermophilum* cell. In another most preferred embodiment, the filamentous fungal host cell is a *Neurospora crassa* cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the Trichoderma cell is a *Trichoderma harzianum, Trichoderma koningii, Trichoderma longibrachiatum, Trichoderma reesei* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81:1470–1474. A suitable method of transforming Fusarium species is described by Malardier et al., 1989, *Gene* 78: 147–156 or in copending U.S. Ser. No. 08/269,449, incorporated herein by reference. Yeast may be transformed using the procedures described by Becker and Guarente, In Abelson, J. N. and Simon, M. I., editors, Guide to Yeast Genetics and Molecular Biology, Methods in Enzymology, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920. Maimmalian cells may be transformed by direct uptake using the calcium phosphate precipitation method of Graham and Van der Eb (1978, *Virology* 52: 546).

Methods of Production

The present invention also relates to recombinant methods for producing a polypeptide of the present invention comprising (a) cultivating a host cell under conditions conducive to expression of the polypeptide; and (b) recovering the polypeptide.

In these methods, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the, polypeptide to be expressed and/or isolated. The cultivation takes place in a suitable nutrient medium comprising carbon and nitrogen sources and inorganic salts, using procedures known in the art (see, e.g., references for bacteria and yeast; Bennett, J. W. and LaSure, L., editors, *More Gene Manipulations in Fungi*, Academic Press, California, 1991). Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it is recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide. The production of tripeptide aminopeptidase activity can be determined by any method known in the art and include, e.g., o-phthaldialdehyde together with dithiothreitol to monitor the liberation of free amino acids under enzymatic hydrolysis according to the procedure of Roth, 1971, *Analytical Chemistry* 43: 880.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation. The recovered polypeptide may then be further purified by a variety of chromatographic procedures, e.g., ion exchange chromatography, gel filtration chromatography, affinity chromatography, or the like.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J.-C. Jarnson and Lars Ryden, editors, VCH Publishers, New York, 1989).

Uses

The polypeptides of the present invention may be used in numerous applications including debittering or enhancing the degree of hydrolysis of protein hydrolysates, flavor development through hydrolysis of a protein, degradation of undesirable peptides, and enzymatic synthesis of peptides. The use of peptidases in these and other applications are well established in the art.

While the presence of tripeptidyl aminopeptidase in protein products susceptible to tripeptidyl aminopeptidase hydrolysis may be considered undesirable due to the resultant reduced stability of said products, the use of the purified tripeptidyl aminopeptidase of the invention for controlled destabilization of protein products may be advantageous. For instance, it is contemplated that the purified tripeptidyl aminopeptidase of the invention may be used for the deactivation of enzymes after they have exerted their desired effect, and thus function as a "killer enzyme". Such deactivation is conventionally accomplished by thermoinactivation, but the process may also result in a loss of activity of the protein of interest. In some cases, it is necessary to remove the undesirable enzyme activity through additional purification procedures. Therefore, use of tripeptidyl aminopeptidase for the inactivation of thermophilic enzymes may be particularly advantageous.

An example of such use of tripeptidyl aminopeptidase is in the deactivation of amyloglucosidase, which is used for starch liquefaction. In current practice, the enzyme is deactivated by heating the reaction mixture to high temperatures (80–85° C.). The equivalent may be achieved at lower temperatures by first adding TPAP, preferably in a batch process after amyloglucosidase has hydrolyzed dextrins to glucose. Complete inactivation of amyloglucosidase would then only require increasing the temperature to about 66° C. for a short period.

Another example where tripeptidyl aminopeptidase inactivation of amyloglucosidase may be desirable is in the fermentation of beer, such as low calorie beer. In the normal beer fermentation procedure, amyloglucosidase is inactivated by pasteurization. It is contemplated that by adding tripeptidyl aminopeptidase to reduce the thermosilability of the used amyloglucosidase, a lower temperature would be required for pasteurization of the beer product. This treatment could result in improved organoleptic characteristics of beer.

Furthermore, a purified tripeptidyl aminopeptidase of the invention may be useful for a number of purposes in which a specific cleavage of tripeptide sequences is desirable. For instance, there are some proteins or peptides which are synthesized in the form of inactive precursors comprising a number of additional amino acid residues at the N-terminal of the mature protein. Tripeptidyl aminopeptidase could provide the necessary post-translational processing to activate such precursor proteins.

Removal or Reduction of TPAP Activity

The identification of TPAP as a destabilizing factor in microbially produced protein products may have important consequences for the production of a large number of different protein products. As demonstrated by the present inventors, even minor amounts of TPAP present in a protein product may result in a reduced stability of said product. Accordingly, by the present invention it is possible to construct production strains of commercial value which have a reduced TPAP producing capability.

The reduction of TPAP production or activity from a TPAP producing cell may be conveniently accomplished by modification or inactivation of a DNA sequence present in said cell and necessary for expression of TPAP. The DNA sequence to be modified or inactivated may be, for example, a DNA sequence encoding TPAP or a part thereof essential for exhibiting TPAP activity, or the sequence may have a regulatory unction required for the expression of TPAP from a TPAP encoding DNA sequence. An example of a regulatory sequence may be a promoter sequence or a functional part thereof, i.e. a part which is sufficient for affecting expression of TPAP.

The modification or inactivation of the DNA sequence may be performed by subjecting the TPAP producing cell to mutagenesis and selecting for cells in which the TPAP producing capability has been reduced. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethlil methane sulphonate (EMS), sodium bisulphite, fonmic acid, and nucleotide analogues.

When such agents are used, the mutagenesis is typically performed by incubating the cell to be mutagenized in the presence of the mutagenizing agent of choice under suitable conditions, and selecting for cells showing a reduced TPAP production.

The modification or inactivation of TPAP production may be accomplished by introduction, substitution or removal of one or more nucleotides irn the TPAP encoding sequence or a regulatory element required for the transcription or translation thereof. For example, nucleotides may be inserted or removed so as to result in the introduction of a stop codon, the removal of the start codon or a change of the open reading frame. The modification or inactivation of the TPAP encoding sequence or a regulatory element thereof may be accomplished by site-directed mutagenesis or PCR generated mutagenesis in accordance with methods known in the art. Although, in principle, the modification may be performed in vivo, i.e. directly on the cell expressing the TPAP gene to be modified, it is presently preferred that the modification be performed in vitro as exemplified below.

An example of a convenient way to inactivate or reduce the TPFAP production of a host cell of choice is based on techniques of gene replacement or gene interruption. For instance, in the gene interruption method, a DNA sequence corresponding to the endogenous gene or gene fragment of interest is mutagenized in vitro. Said DNA sequence thus encodes a defective gene which is then transformed into the host cell. By homologous recombination the defective gene replaces the endogenous gene or gene fragment. It may be desirable that the defective gene or gene fragment also encodes a marker which may be used for selection of transformants in which the TPAP gene has been modified or destroyed.

Alternatively, the modification or inactivation of the DNA, sequence may be performed by established anti-sense techniques using a nucleotide sequence complementary to the TPAP encoding sequence, e.g. the nucleotide sequence (f) described above. More specifically, the TPAP production from a TPAP producing cell may be reduced or eliminated by introducing a nucleotide sequence complementary to the TPAP encoding sequence which may be transcribed in the cell and is capable of hybridizing to TPAP mRNA produced in the cell. Under conditions allowing the complementary anti-sense nucleotide sequence to hybridize to the TPAP mRNA the amount of TPAP translated is thus reduced or eliminated.

The TPAP-deficient mutants so created are particularly useful as host cells for the expression of heterologous proteins. In the present context the term "heterologous proteins" is intended to indicate a protein which is not native to the host cell, a native protein in which modifications have been made to alter the native sequence, or a native protein whose expression is quantitatively altered as a result of a manipulation of the host cell by recombinant DNA techniques.

It is preferred that the TPAP producing cell to be modified in accordance with the present invention is of microbial origin, for example, a fungal strain which is suitable for the production of desired protein products, either homologous or heterologlous to the cell. Cells of the fungal genera Aspergillus, Trichoderna and Fusarium are examples of preferred production cells. Accordingly, the cell to be modified in accordance with the present invention is preferably a cell of an Aspergillus species, in particular a cell of A. niger, A. oryzae, A. japonicus, A. foetidus or A. nidulans or a cell of a Trichoderma species, e.g. T. reesei, T. longibrachiatum or T. harzianum, or a cell of a Fusarium species, e.g. F. oxysporum, F. graminearum or F. solani.

In a specific embodiment of the invention the cell to be modified is from a strain of A. niger or A. oryzae which is used for the production of enzymes such as AMG.

In a further aspect the invention relates to a method of preparing a product essentially free from TPAP activity, in which the method comprises transforming a host cell suitably modified as described above to exhibit a reduced or no TPAP producing capability with a DNA sequence encoding the protein of interest, culturing the transformed cell under suitable conditions for expression of the protein product, and recovering the product from the culture.

In an alternative aspect the invention relates to a method of preparing a protein product essentially free from TPAP activity, wherein the product is encoded by a DNA sequence present in a TPAP expressing cell. The method comprises modifying or inactivating a DNA sequence present and necessary for the expression of TPAP in said cell as described above, and subsequently culturing the cell under suitable conditions for expression of the product, and recovering the product from the culture.

In a still further aspect the invention relates to a method of preparing a product essentially free from TPAP by fermentation of a TPAP producing cell which also produces the protein product of interest. The method comprises adding an effective amount of an agent capable of inhibiting TPAP activity to the fermentation broth either during or after the fermentation has been completed, recovering the product of interest from the fermentation broth, and optionally subjecting the recovered product to further purification. This method is further illustrated in the examples below.

In a still further alternative aspect the invention relates to a method of preparing a product essentially free from TPAP activity, wherein the protein product of interest is encoded by a DNA sequence present in a TPAP expressing cell. The method comprises cultivating the TPAP expressing cell encoding the product under conditions permitting the expression of the product, subjecting the resultant culture broth to a combined pH and temperature treatment so as to reduce the TPAP activity substantially, and recovering the product from the culture broth. Alternatively, the combined pH and temperature treatment may be performed on an enzyme preparation recovered from the culture broth. The combined pH and temperature treatment may optionally be used in combination with a treatment with a TPAP inhibitor.

In accordance with this aspect of the invention it is possible to remove at least 60% of the TPAP activity, preferably at least 75% of the activity, more preferably at least 85% of the activity, still more preferably at least 95% of the activity, and most preferably at least 99% of the TPAP activity. It is contemplated that a complete removal of TPAP activity may be obtained by use of this method.

The combined pH and temperature treatment is preferably carried out at a pH in the range of 6.5–7 and a temperature in the range of 25–40° C. for a sufficient period of time for obtaining the desired effect. Typically, 0.5–1 hour is sufficient for obtaining the desired effect.

The methods used for cultivation and purification of the product of interest may be performed by methods known in the art, e.g. as described herein above.

The methods of the invention for producing an essentially TPAP-free product is of particular interest in the production of eukaryotic proteins, in particular fungal proteins such as enzymes. The enzyme product may be selected from, e.g., an arnylolytic enzyme, a lipolytic enzyme, a proteolytic enzyme, a cellulytic enzyme, an oxidoreductase or a plant cell-wall degrading enzyme. Examples of such enzymes include AMG, amylase, lipase, cutinase, esterase, cellulase, hemicellulase, protease, peroxidase, laccase, phenoloxidase, catalase, glucose oxidase, phytase, lyase, pectinase, glucosidase, mannosidase, isomerase, invertase, trasferase, ribonuclease, galactosidase, transglutaminase and chitinase. The TPAP-deficient cells may also be used to express heterologous proteins of pharmaceutical interest such as hormones, growth factors, receptors, and the like.

It will be understood that the term "eukaryotic proteins" is intended to include not only native proteins, but also those proteins, e.g. enzymes, which have been modified by amino acid substitutions, deletions or additions, or other such modifications to enhance activity, thermostability, pH tolerance and the like.

In a further aspect the invention relates to a protein product essentially free from TPAP activity which is produced by the method of the invention.

The present invention is further described by the following examples which should not be construed as limiting the scope of the invention.

EXAMPLES

Materials

Chemicals used as buffers and substrates were commercial products of at least reagent grade.

Example 1

RNA Isolation

Aspergillus oryzae strain 1568 (ATCC 20386) was cultivated in a fermentation tank in a medium comprised of 7.5 g of potato starch, 10 g of soy bean me,al, 2 g of $KH_2PO_4$, 5 g of $Na_2HPO_4$-$2H_2O$, and 0.1 g of $ZnSO_4$-$7H_2O$ per liter. A two liter sample was taken five days of growth at 30° C., and the mycelia were collected, frozen in liquid $N_2$, and stored at –80° C. Total RNA was prepared from the frozen, powdered mycelia of Aspergillus oryzae 1568 by extraction with guanidinium thiocyanate followed by ultracentrifugation through a 5.7 M cesium chloride cushion (Chirgwin et al., 1979, Biochemistry 18: 5294–5299). Poly(A)+ RNA was isolated by oligo(dT)-cellulose affinity chromatography according to Aviv and Leder (1972, Proceedings of the National Academy of Sciences USA 69: 1408–1412).

Example 2

Construction of a cDNA Library

Double-stranded cDNA was synthesized from 5 μg of Aspergillus oryzae 1568 poly(A)+ RNA of Example 1 using the procedure described by Gubler and Hoffinan (1983, Gene 25: 263–269) and Sambrook et al. (1989, Molecular Cloning: A Laboratory Manual, Cold Spring Harbor Press, Cold Spring Harbor, N.Y.), except that an oligo(dT)-NotI anchor primer, instead of an oligo(dT)12-18 primer, was used in the first strand reaction. After synthesis, the cDNA was treated with Mung bean nuclease (Life Technologies, Gaithersburg, Md.), blunt-ended with T4 DNA polymerase (Boehringer Mannheim, Indianapolis, Ind.), and ligated to non-palindromic BstXI adaptors (Inrritrogen, San Diego, Calif.), using about 50-fold molar excess of the adaptors. The adapted cDNA was digested with NotI, size-fractionated for 1.2-3.0 kb cDNAs by agarose gel electrophoresis, and ligated into BstXIlNotI cleaved pYES2.0 vector (Invitrogen, San Diego, Calif.). The ligation mixture was transformed into electrocompetent E. coli DH10B cells (Life Technologies, Gaithersburg, Md.) according to the manufacturer's instructions. The library consisting of $1 \times 10^6$ independent clones was stored as individual pools (25,000–30,000 colony forming units/pool) in 20% glycerol at –80° C., and as double stranded cDNA arid ligation mixture at –20° C.

Example 3

Genomic DNA Extraction

Aspergillus oryzae 1568 was grown in 25 ml of 0.5% yeast extract-2% glucose (YEG) medium for 24 hours at 37° C. and 250 rpm. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia preparation which was subsequently frozen in liquid nitrogen. The frozen mycelia preparation was ground to a fine powder in an electric coffee grinder, and the powder was added to a disposable plastic centrifuge tube containing 20 ml of TE buffer and 5 ml of 20% w/v sodium dodecylsulfate (SDS). The mixture was gently inverted several times to ensure mixing, and extracted twice with an equal volume of phenol:chloroform: isoamyl alcohol (25:24: 1 v/v/v). Sodium acetate (3 M solution) was added to the extracted sample to a final concentration of 0.3 M followed by 2.5 volumes of ice cold ethanol to precipitate the DNA. The tube was centrifuged at 15,000×g for 30 minutes to pellet the DNA. The DNA pellet was allowed to air-dry for 30 minutes before resuspension in 0.5 ml of TE buffer. DNase-free ribonuclease A was added to the resuspended DNA pellet to a concentration of 100 µg/ml tnd the mixture was then incubated at 37° C. for 30 minutes Proteinase K (200 µg/ml) was added and the tube was incubated an additional one hour at 37° C. Finally, the sample was extracted twice with phenol:chloroform:isoamyl alcohol and the DNA precipitated with etharnol. The precipitated DNA was washed with 70% ethanol, dried under vacuum, resuspended in TE buffer, and stored at 4° C.

Example 4

PCR Amplification of Aspergillus oryzae 1568 Tripeptide Aminopeptidase

Based on the amino acid sequences of the Aspergillus oryzae 1568 tripeptide aminopeptidase partial peptides described in WO 96/14404, the degenerate oligonucleotide primers shown below were synthesized with an Applied Biosystems Model 394 DNA/RNA Synthesizer, according to the manufacturer's instructions, for use to PCR amplify tripeptide aminopeptidase gene fragments from Aspergillus oryzae 1568:

Forward primer:
  5'-TAYAAYATHGGIGAYTAYCARGCYGAYGC-3' (SEQ ID NO:3)
Reverse primer:
  5'-GCIACIGCYTGRTTYTGCCAYTCIGG-3' (SEQ, ID NO:4)
  (R=A or G, Y=C or T, N=G or A or C or T, H=A or C or T, I=Inosine)

Amplification reactions (100 µl) were prepared using approximately 1 µg of genomic DNA isolated from an Aspergillus oryzae 1568 as described in Example 3 as the template. Each reaction contains the following components: 1 µg genomic DNA, 40 pmol forward primer, 40 pmol reverse primer, 200 µM each of dATP, dCTP, dGTP, and dTTP, 1× Taq polymerase buffer (Perkin-Elmer Corp., Branchburg, N.J.), and 2.5 UrLits of Taq polymerase (Perkin-Elmer Corp., Branchburg, N.J.). The reactions were incubated in a Perkin-Elmer Model 480 Thermal Cycler programmed as follows: Cycle 1–95° C. for 5 minutes, 45° C. for 2 minutes, and 67° C. for 2 minutes; and Cycles 2–30 –95° C. for 2 minutes; 45° C. for one minute, and 67° C. for 2 minutes. The reaction products were isolated an a 1% agarose gel (Eastman Kodak, Rochester, N.Y.). The 760 bp product band was excised from the gel and purified using GenElute spin columns (Supelco, Bellefonte, Pa.) according to the manufacturer's instructions. The purified PCR products were subsequently cloned into a pCRII vector (Invitrogen, San Diego, Calif.) and the DNA sequences were determined using lac forward and reverse primers (New England BioLabs, Beverly, Mass.).

A tripeptide aminopeptidase I gene segment (760 bp) consisting of 145 codons and interrupted by a 53 bp intron was amplified from Aspergillus oryzae 1568 with the tripeptide aminopeptidase-specific PCR primers described above. DNA sequence analysis shows that the amplified gene segment encodes a portion of the corresponding Aspergillus oryzae 1568 tripeptide aminopeptidase I gene. The tripeptide aminopeptidase I gere segment was used to probe an Aspergillus oryzae 1568 cDNA library.

Example 5

Identification of Tripeptide Aminopeptidase I Clones

The Aspergillus oryzae 1568 cDNA library was plated on Luria plus 50 µg/ml carbenicillin agar plates. Colony lifts (Maniatis et al., 1982, Molecular Cloning, A Laboratory Manual, Cold Spring Harbor Press, Cold Spring Harbor, N.Y.) were performed on approximately 5,000 colonies and the DNA was cross-linked onto membranes (Hybond N+, Amersham, Arlington Heights, Ill.) using a UV Stratalinker (Stratagene, La Jolla, Calif.). The membranes were soaked for three hours at 45° C. in a hybridization solution containing 5× SSPE, 0.3% SDS, 50% formamide, and 10 mg/ml of denatured and sheared herring sperm DNA. The tripeptide aminopeptidase I gene fragment isolated from the Aspergillus oryzae 1568 as described in Example 3 was radiolabeled using the Random Primed DNA Labeling Kit (Boehringer Mannheim, Mannheim, Germany), denatured by adding NaOH to a final concentration of 0.1 M, and added to the hybridization solution at an activity of approximately 1×10$^6$ cpm per ml of hybridization solution. The mixture was incubated overnight at 45° C. in a shaking water bath. Following incubation, the membranes were washed once in 2× SSC with 0.2% SDS at 55° C. followed by two washes in 2× SSC at the same temperature. The membranes were dried on blotting paper for 15 minutes, wrapped in SaranWrap™, and exposed to X-ray film overnight at -70° C. with intensifying screens (Kodak, Rochester, N.Y.).

Two colonies, designated E. coli DH5α clones EJG13A and EJG,13B, produced strong hybridization signals with the probe. The two colonies were inoculated into three ml of LB plus 50 µg/ml carbenicillin medium and grown overnight at 37° C. Miniprep DNA was prepared from each of these clones using the Wizard 373 DNA Purification Kit (Promega, Madison, Wis.). The tripeptide aminopeptidase encoding plasmids (pEJG13) were confirmed by DNA sequencing.

Example 6

DNA Sequence Analysis of Aspergillus oryzae 1568 Tripeptide Aminopeptidase I Gene DNA sequencing of the tripeptide aminopeptidase I gene contained on pEJG13 in E. coli DH5α EJG13A described in Example 5 was performed with an Applied Biosystems Model 373A Automated DNA Sequencer (Applied Biosystems, Inc., Foster City, Calif.) on both strands using the primer walking technique with dye-terminator chemistry (Giesecke et al., 1992, Journal of Virology Methods 38: 47–60). Oligonucleotide sequencing primers were designed to complementary sequences in the tripeptide aminopeptidase I gene and were synthesized on an Applied Biosystems Model 394 DNA/RNA Synthesizer according to the manufacturer's instructions.

The nucleotide sequence of the gene encoding the Aspergillus oryzae 1568 tripeptide aminopeptidase I is shown in FIG. 1 (SEQ ID NO:1). Sequence analysis of the cloned insert revealed a large open reading frame of 1800 nucleotides (excluding the stop codon) encoding a protein of 600 amino acids sequence (SEQ ID NO:2). The G+C content of this open reading frame is 59.4%. Based on the rules of van Heijne (van Heijne, 1984, Journal of Molecular Biology 173: 243–251), the first 21 amino acids likely comprise a secretory signal peptide which directs the nascent polypeptide into the endoplasmic reticulum. The next 179 amino acids likely comprise a propeptide.

The amino acid sequences of the partial peptides derived from the purified tripeptide aminopeptidase I as described in WO 96/14404 are boxed in FIG. 1 and are consistent with those found in the deduced amino acid sequence (SEQ ID NO:2) of the Aspergillus oryzae 1568 tripeptide aminopeptidase cDNA.

Using the Clustal alignment program (Higgins, 1989, supra) to compare the deduced amino acid sequence of the *Aspergillus oryzae* 1568 tripeptide aminopeptidase to that of the *Aspergillus niger* tripeptide aminopeptidase (SEQ ID NO:5), a 69.7%) identity is observed (FIG. 2).

Example 7

Construction of pEJG17 for Expression of the *Aspergillus oryzae* 1568 Tripeptide Aminopeptidase I Gene in Fusatium Two synthetic oligonucleotide primers shown below were designed to PCR amplify the *Aspergillus oryzae* 1568 tripeptideaminopeptidase I gene coding sequence from plasmid pEJG13 (*E. coli* DH5α EJG13A clone) for subcloning and expression in a Fusarium host.

```
                         SwaI
Forward Primer:  5'-GGGATTTAAATATGTTCTTCAGTCGT-3'  (SEQ ID NO:6)

PacI
Reverse primer:  5'-GGGTTAATTAATTAGTTGCCAAGGGC-3'  (SEQ ID NO:7)
```

In order to facilitate the subcloning of the gene fragment into an expression vector designated pDM181 (FIG. 3), SwaI and PacI restriction enzyme sites were introduced at the 5' and 3' end of the gene, respectively. The vector pDM181 contained the *Fusarium oxysporum* (SP 387) trypsin-like protease promoter and terminator (WO 96/00787) as regulatory sequences. The plasmid also contained the bar gene as a selectable marker for fungal transformations.

One hundred picomoles of each of the primers above were used in a PCR reaction containing 52 ng of pEJG13, 1× Pwo Buffer (Boehringer Mannheim, Indianapolis, Ind.), 1 mM each dATP, dTTP, dGTP, and dCTP, and 2.5 units of PwoI (Boehringer Mannheim, Indianapolis, Ind.). The amplification conditions were one cycle at 94° C. for 2 minutes, 50° C. for 30 seconds, and 72° C. for 1 minute; 9 cycles each at 94° C. for 15 seconds, 50° C. for 30 seconds, and 72 ° C. for 1 minute; 15 cycles each at 94° C. for 15 seconds, 55° C. for 30 seconds, and 72° C. for 1 minute plus 20 seconds for each additional cycle; one cycle at 94° C. for 15 seconds, 55° C. for 30 seconds, and 72° C. for 7 minutes; and a soak cycle at 4° C. The amplified 2866 bp DNA fragment was purified by gel electrophoresis and cut with restriction endonucleases SwaI and PacI (using conditions specified by the manufacturer). The cut fragment was cloned into pDM181 (FIG. 3) that had been previously cut with SwaI and PacI resulting in the expression plasmid pEJG17 (FIG. 4) in which transcription of the tripeptide aminopeptidase I gene was under the control of the the *Fusarium oxysporum* trypsin-like protease promoter. The plasmid pEJG17 was transformed into *E. coli* DH5α cells. The *E. coli* transformant containing the pEJG17 plasmid was isolated and plasmid DNA was prepared according to procedures described by Sambrook et al., 1989, supra.

Example 8

Transformation of Fusatium

Fusarium strain CC1-3, a highly branched morphological mutant of Fusarium strain A3/5 (ATCC 20334) was grown in a liquid medium containing Vogel's salts, (Vogel, 1964, *Am. Nature* 98:435–446), 25 mM NaNO$_3$, and 1.5% glucose for 4 days at 28° C. and 150 rpm. Conidia were purified by filtration through 4 layers of cheesecloth and finally through one layer of Miracloth. Conidial suspensions were concentrated by centrifugation. Fifty ml of YPG medium comprised of 1% yeast extract, 2% bactopeptone, and 2% glucose were inoculated with approximately 10$^8$ conidia, and incubated for 14 hours at 24° C. and 150 rpm. Resulting hyphae were trapped on a sterile 0.4 μm filter and washed successively with sterile distilled water and 1.0 M MgSO$_4$. The hyphae were resuspended in 10 ml of NOVOZYM 234™ solution (2–10 mg/ml in 1.0 M MgSO$_4$) and digested for 15–30 minutes at 34° C. with agitation at 80 rpm. Undigested hyphal material was removed from the resulting protoplast suspension by successive filtration through 4 layers of cheesecloth and through Miracloth. Twenty ml of 1 M sorbitol were combined with the protoplast solution. After mixing, the protoplasts were pelleted by centrifugation and washed successively by resuspension and centrifugation in 20 ml of 1 M sorbitol and in 20 ml of STC (0.8 M sorbitol, 0.05 M Tris pH 8.0, 0.05 M CaCl$_2$). The washed protoplasts were resuspended in 4 parts STC and 1 part SPTC (0.8 M sorbitol, 40% PEG 4000, 0.05 M Tris pH 8.0, 0.05 M CaCl$_2$) at a concentration of 5×10$^7$/ml. One hundred μl of protoplast suspension were added to 5 μg of pEJG17 in polypropylene tubes (17×100 mm), mixed and incubated on ice for 30 minutes. One ml of SPTC was mixed gently into the protoplast suspension and incubation was continued at room temperature for 20 minutes. 12.5 ml of molten solution (cooled to 40° C.) consisting of 1*33 Vogel's salts (Vogel, 1964, Am. Nature* 98:435–446), 25 mM NaNO$_3$, 0.8 M sucrose and 1% low melting agarose (Sigma Chemical Company, St. Louis, Mo.) were mixed with the protoplasts and then plated onto an empty 100 mm petri plate. Incubation was continued at room temperature for 10 to 14 days. After incubation at room temperature for 24 hours, 12.5 ml of the identical medium plus 10 mg of basta (Hoechst Schering, Rodovre, Denmark) per ml were overlayed onto the Petri plate. Basta was extracted twice with phenol:chloroform:isoamyl alcohol (25:24:1), and once with chloroform:isoamyl alcohol (24:1) before use. After two weeks, ten transformants were apparent. A mycelial fragment from the edge of each transformant was transferred to individual wells of a 24 well plate containing Vogel's/BASTA medium. The medium contained 25 g of sucrose, 25 g of Noble agar, 20 mls of 50× Vogel's salts (Vogel, 1964, supra), 25 mM NaNO$_3$, and 10 g of basta per liter. The plate was seated in a plastic bag to maintain moisture and incubated approximately one week at room temperature.

Example 9

Expression of Tripeptide Aminopeptidase I Gene

A mycelial fragment from each of the ten Fusarium CC1-3 transformants described in Example 8 was inoculated into 20 ml of M400Da medium containing 50 g of maltodextrin, 2.0 g of MgSO$_4$-7H$_2$O, 2.0 g of KH$_2$PO$_4$, 4.0 g of citric acid, 8.0 g of yeast extract, 2.0 of urea, and 0.5 ml of trace metals solution per liter and incubated for 7 days at 30° C. and 150 rpm. The medium was adjusted to pH 6.0 with 5 N NaOH. The trace metals solution contained 14.3 g of ZnSO$_4$-7H$_2$O, 2.5 g of CuSO$_4$-5H$_2$O, 0.5 g of NiCl$_2$-6H$_2$O, 13.8 g of FeSO$_4$-7H$_2$O, 8.5 g of MnSO$_4$-H$_2$O, and 3.0 g of citric acid per liter. Aliquots were taken at days 5, 6, and 7 and assayed for tripeptide aminopeptidase activity according to the following assay. The untransformed host was also run as a control.

The stock substrate solution was prepared by dissolving 10 mg of Phe-Pro-Ala-p-nitrophenylacetate (Bachem, Inc., Torrance, Calif.) in 100 μl of DMSO and diluting the solution 50-fold in 50 mM sodium phosphate pH 7.5 buffer. The tripelptide aminopeptidase aliquots were diluted in 50 mM sodium phosphate pH 7.5 buffer. Then in a 96 well plate, 100 μl of each enzyme solution is mixed with 100 μl of the Phe-Pro-Ala-p-nitrophenylacetate solution and the absorbance at 405 nm is measured over a 3 minute period with a Molecular Devices ThermoMax microplate reader (Molecular Devices, Sunnyvale, Calif.).

The results of the tripeptide aminopeptidase assays demonstrated that 8 of the 10 transformants produced activity.

Deposit of Biological Materials

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
| --- | --- | --- |
| *E. coli* DH5α pEJG13 | NRRL B-21617 | August 28, 1996 |

What is claimed is:

1. An isolated polypeptide having tripeptidyl aminopeptidase activity selected from the group consisting of:
   (a) a tripeptidyl aminopeptidase having an amino acid sequence of amino acids 201–600 of SEQ ID NO:2;
   (b) a tripeptidyl aminopeptidase endogenous to an Aspergillus strain, which is encoded by a nucleic acid sequence which hybridizes under high stringency conditions with one or more of (i) nucleotides 621–1803 of SEQ ID NO:1 and (ii) its complementary strands;
   (c) an allelic form of (a) or (b); and
   (d) a fragment of (a), (b), or (c).

2. The polypeptide of claim 1 which has an amino acid sequence of amino acids 201–600 of SEQ ID NO:2.

3. The polypeptide of claim 1 which is endogenous to a strain of A. oryzae.

4. The polypeptide of claim 1 which is endogenous to a strain of A. niger.

5. The polypeptide of claim 1 which is endogenous to a strain of A. japonicus.

6. The polypeptide of claim 1 which is endogenous to a strain of A. foetidus.

7. An isolated nucleic acid sequence encoding a polypeptide of claim 1.

8. The nucleic acid sequence of claim 7, wherein the nucleic acid sequence hybridizes under high stringency conditions with (i) nucleotides 621–1803 of SEQ ID NO:1 or (ii) its complementary strand; or a fragment thereof.

9. The nucleic acid sequence of claim 7, wherein the nucleic acid sequence hybridizes under high stringency conditions to (i) the nucleic acid sequence of SEQ ID NO:1 or (ii) its complementary strand.

10. The nucleic acid sequence of claim 8, wherein the nucleic acid sequence is obtained from Aspergillus oryzae.

11. The nucleic acid sequence of claim 7, wherein the nucleic acid sequence encodes the amino acid sequence of amino acids 201–600 of SEQ ID NO:2.

12. The nucleic acid sequence of claim 11, wherein the nucleic acid sequence is nucleotides 621–1803 of SEQ ID NO:1.

13. The nucleic acid sequence of claim 7, which comprises the tripeptide aminopeptidase coding region nucleic acid sequence contained in the plasmid pEJG13 which is contained in Escherichia coli NRRL B-21617.

14. A nucleic acid construct comprising the nucleic acid sequence of claim 7 operably linked to one or more control sequences which direct the expression of the polypeptide having tripeptide aminopeptidase activity in a suitable expression host.

15. A recombinant expression vector comprising the nucleic acid construct of claim 14.

16. The vector of claim 15, further comprising a selectable marker.

17. A recombinant host cell comprising the nucleic acid construct of claim 14.

18. The cell of claim 17, wherein the nucleic acid construct is contained on a vector.

19. The cell of claim 18, wherein the nucleic acid construct is integrated into the host cell genome.

20. The cell of claim 17, wherein the host cell is a fungal cell.

21. The cell of claim 20, wherein the fungal cell is a filamentous fungal cell.

22. The cell of claim 21, wherein the filamentous fungal cell is a cell of a species of Acremonium, Aspergillus, Fusarium, Humicola, Mucor, Myceliophthora, Neurospora, Penicillium, Thielavia, Tolypocladium, or Trichoderma.

23. The cell of claim 20, wherein the fungal cell is a yeast cell.

24. The cell of claim 23, wherein the yeast cell is a cell of a species of Candida, Kluyveromyces, Pichia, Saccharomyces, Schizosaccharomyces or Yarrowia.

25. A method for producing a polypeptide having tripeptide aminopeptidase activity comprising (a) cultivating the host cell of claim 17 under conditions conducivie for production of the polypeptide; and (b) recovering the polypeptide.

26. A method for producing a mutant of a parent cell, which comprises disrupting or deleting the nucleic acid sequence of claim 7 or a control sequence thereof, which results in the mutant producing less of the polypeptide having tripeptide aminopeptidase activity than the parent cell.

27. A cell having a mutation relative to a parent cell, wherein the mutation comprises a disruption or deletion of the nucleic acid sequence of claim 7, wherein the disruption or deletion results in the mutant producing less of the polypeptide having tripeptide aminopeptidase activity than the parent cell.

28. The mutant of claim 27, which further comprises a nucleic acid sequence encoding a heterologous protein.

29. A method for producing a heterologous protein comprising (a) culturing the mutant of claim 28 under conditions conducive for the expression of the heterologous protein; and (b) recovering the protein from the culture.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 1803 base pairs
      (B) TYPE: nucleic acid
      (C) STRANDEDNESS: single
      (D) TOPOLOGY: linear (ii) MOLECULE TYPE: Genomic DNA (ix) FEATURE:
      (A) NAME/KEY: Coding Sequence
      (B) LOCATION: 1...1800
      (D) OTHER INFORMATION:

(xi) SEQUENCE DESCRIPTION: SEQ ID NO:1:

```
ATG TTC TTC AGT CGT GGA GCG CTT TCG CTC GCA GTG CTT TCA CTG CTC      48
Met Phe Phe Ser Arg Gly Ala Leu Ser Leu Ala Val Leu Ser Leu Leu
 1               5                  10                  15

AGC TCC TCC GCC GCA GGG GAG GCT TTT GAG AAG CTG TCT GCC GTT CCA      96
Ser Ser Ser Ala Ala Gly Glu Ala Phe Glu Lys Leu Ser Ala Val Pro
                20                  25                  30

AAG GGA TGG CAC TAT TCT AGT ACC CCT AAA GGC AAC ACT GAG GTT TGT     144
Lys Gly Trp His Tyr Ser Ser Thr Pro Lys Gly Asn Thr Glu Val Cys
            35                  40                  45

CTG AAG ATC GCC CTC GCG CAG AAG GAT GCT GCT GGG TTC GAA AAG ACC     192
Leu Lys Ile Ala Leu Ala Gln Lys Asp Ala Ala Gly Phe Glu Lys Thr
        50                  55                  60

GTC TTG GAG ATG TCG GAT CCC GAC CAC CCC AGC TAC GGC CAG CAC TTC     240
Val Leu Glu Met Ser Asp Pro Asp His Pro Ser Tyr Gly Gln His Phe
65                  70                  75                  80

ACC ACC CAC GAC GAG ATG AAG CGC ATG CTT CTT CCC AGA GAT GAC ACC     288
Thr Thr His Asp Glu Met Lys Arg Met Leu Leu Pro Arg Asp Asp Thr
                85                  90                  95

GTT GAT GCC GTT CGA CAA TGG CTC GAA AAC GGC GGC GTG ACC GAC TTT     336
Val Asp Ala Val Arg Gln Trp Leu Glu Asn Gly Gly Val Thr Asp Phe
                100                 105                 110

ACC CAG GAT GCC GAC TGG ATC AAC TTC TGT ACT ACC GTC GAT ACC GCG     384
Thr Gln Asp Ala Asp Trp Ile Asn Phe Cys Thr Thr Val Asp Thr Ala
            115                 120                 125
```

```
AAC AAA CTC TTG AAT GCC CAG TTC AAA TGG TAC GTC AGC GAT GTG AAG         432
Asn Lys Leu Leu Asn Ala Gln Phe Lys Trp Tyr Val Ser Asp Val Lys
    130                 135                 140

CAC ATC CGC CGT CTC AGA ACA CTG CAG TAC GAC GTC CCC GAG TCG GTC         480
His Ile Arg Arg Leu Arg Thr Leu Gln Tyr Asp Val Pro Glu Ser Val
145                 150                 155                 160

ACC CCT CAC ATC AAC ACC ATC CAA CCG ACC ACC CGT TTT GGC AAG ATT         528
Thr Pro His Ile Asn Thr Ile Gln Pro Thr Thr Arg Phe Gly Lys Ile
                165                 170                 175

AGC CCC AAG AAG GCC GTT ACC CAC AGC AAG CCC TCC CAG TTG GAC GTG         576
Ser Pro Lys Lys Ala Val Thr His Ser Lys Pro Ser Gln Leu Asp Val
        180                 185                 190

ACC GCC CTT GCT GCC GCT GTC GTT GCA AAG AAC ATC TCG CAC TGT GAT         624
Thr Ala Leu Ala Ala Ala Val Val Ala Lys Asn Ile Ser His Cys Asp
            195                 200                 205

TCT ATC ATT ACC CCC ACC TGT CTG AAG GAG CTT TAC AAC ATT GGT GAT         672
Ser Ile Ile Thr Pro Thr Cys Leu Lys Glu Leu Tyr Asn Ile Gly Asp
210                 215                 220

TAC CAG GCC GAT GCA AAC TCG GGC AGC AAG ATC GCC TTC GCC AGC TAT         720
Tyr Gln Ala Asp Ala Asn Ser Gly Ser Lys Ile Ala Phe Ala Ser Tyr
225                 230                 235                 240

CTG GAG GAG TAC GCG CGC TAC GCT GAC CTG GAG AAC TTT GAG AAC TAC         768
Leu Glu Glu Tyr Ala Arg Tyr Ala Asp Leu Glu Asn Phe Glu Asn Tyr
                245                 250                 255

CTT GCT CCC TGG GCT AAG GGC CAG AAC TTC TCC GTT ACC ACC TTC AAC         816
Leu Ala Pro Trp Ala Lys Gly Gln Asn Phe Ser Val Thr Thr Phe Asn
        260                 265                 270

GGC GGT CTC AAT GAT CAG AAC TCC TCG TCC GAT AGC GGT GAG GCC AAC         864
Gly Gly Leu Asn Asp Gln Asn Ser Ser Ser Asp Ser Gly Glu Ala Asn
            275                 280                 285

CTG GAC CTG CAG TAC ATT CTT GGT GTC AGC GCT CCA CTG CCC GTT ACT         912
Leu Asp Leu Gln Tyr Ile Leu Gly Val Ser Ala Pro Leu Pro Val Thr
290                 295                 300

GAA TTC AGC ACC GGA GGC CGT GGT CCC CTC GTT CCT GAT CTG ACC CAG         960
Glu Phe Ser Thr Gly Gly Arg Gly Pro Leu Val Pro Asp Leu Thr Gln
305                 310                 315                 320

CCG GAT CCC AAC TCT AAC AGC AAT GAG CCG TAC CTT GAG TTC TTC CAG        1008
Pro Asp Pro Asn Ser Asn Ser Asn Glu Pro Tyr Leu Glu Phe Phe Gln
                325                 330                 335

AAT GTG TTG AAG CTC GAC CAG AAG GAC CTC CCC CAG GTC ATC TCG ACC        1056
Asn Val Leu Lys Leu Asp Gln Lys Asp Leu Pro Gln Val Ile Ser Thr
        340                 345                 350

TCC TAT GGA GAG AAC GAA CAG GAA ATC CCC GAA AAG TAC GCT CGC ACC        1104
Ser Tyr Gly Glu Asn Glu Gln Glu Ile Pro Glu Lys Tyr Ala Arg Thr
            355                 360                 365

GTC TGC AAC CTG ATC GCT CAG CTT GGC AGC CGC GGT GTC TCC GTT CTC        1152
Val Cys Asn Leu Ile Ala Gln Leu Gly Ser Arg Gly Val Ser Val Leu
370                 375                 380

TTC TCC TCC GGT GAC TCT GGT GTT GGC GAG GGC TGC ATG ACC AAC GAC        1200
Phe Ser Ser Gly Asp Ser Gly Val Gly Glu Gly Cys Met Thr Asn Asp
385                 390                 395                 400

GGC ACC AAC CGG ACT CAC TTC CCA CCC CAG TTC CCC GCC GCT TGC CCG        1248
Gly Thr Asn Arg Thr His Phe Pro Pro Gln Phe Pro Ala Ala Cys Pro
                405                 410                 415

TGG GTC ACC TCC GTC GGC GCC ACC TTC AAG ACC ACT CCC GAG CGC GGC        1296
Trp Val Thr Ser Val Gly Ala Thr Phe Lys Thr Thr Pro Glu Arg Gly
        420                 425                 430

ACC TAC TTC TCC TCG GGC GGT TTC TCC GAC TAC TGG CCC CGT CCC GAA        1344
Thr Tyr Phe Ser Ser Gly Gly Phe Ser Asp Tyr Trp Pro Arg Pro Glu
            435                 440                 445
```

```
TGG CAG GAT GAG GCC GTG AGC AGC TAC CTC GAG ACG ATC GGC GAC ACT    1392
Trp Gln Asp Glu Ala Val Ser Ser Tyr Leu Glu Thr Ile Gly Asp Thr
    450                 455                 460

TTC AAG GGC CTC TAC AAC TCC TCC GGC CGT GCT TTC CCC GAC GTC GCA    1440
Phe Lys Gly Leu Tyr Asn Ser Ser Gly Arg Ala Phe Pro Asp Val Ala
465                 470                 475                 480

GCC CAG GGC ATG AAC TTC GCC GTC TAC GAC AAG GGC ACC TTG GGC GAG    1488
Ala Gln Gly Met Asn Phe Ala Val Tyr Asp Lys Gly Thr Leu Gly Glu
                485                 490                 495

TTC GAC GGC ACC TCC GCC TCC GCC CCG GCC TTC AGC GCC GTC ATC GCT    1536
Phe Asp Gly Thr Ser Ala Ser Ala Pro Ala Phe Ser Ala Val Ile Ala
            500                 505                 510

CTC CTG AAC GAT GCC CGT CTC CGC GCC GGC AAG CCC ACT CTC GGC TTC    1584
Leu Leu Asn Asp Ala Arg Leu Arg Ala Gly Lys Pro Thr Leu Gly Phe
        515                 520                 525

CTG AAC CCC TGG TTG TAC AAG ACC GGC CGC CAG GGT CTG CAA GAT ATC    1632
Leu Asn Pro Trp Leu Tyr Lys Thr Gly Arg Gln Gly Leu Gln Asp Ile
    530                 535                 540

ACC CTC GGT GCT AGC ATT GGC TGC ACC GGT CGC GCT CGC TTC GGC GGC    1680
Thr Leu Gly Ala Ser Ile Gly Cys Thr Gly Arg Ala Arg Phe Gly Gly
545                 550                 555                 560

GCC CCT GAC GGT GGT CCC GTC GTG CCT TAC GCT AGC TGG AAC GCT ACC    1728
Ala Pro Asp Gly Gly Pro Val Val Pro Tyr Ala Ser Trp Asn Ala Thr
                565                 570                 575

CAG GGC TGG GAT CCC GTC ACT GGT CTC GGA ACT CCC GAT TTC GCC GAG    1776
Gln Gly Trp Asp Pro Val Thr Gly Leu Gly Thr Pro Asp Phe Ala Glu
            580                 585                 590

CTC AAG AAG CTT GCC CTT GGC AAC TAA                                1803
Leu Lys Lys Leu Ala Leu Gly Asn
        595                 600

(2) INFORMATION FOR SEQ ID NO:2:

(i) SEQUENCE CHARACTERISTICS:
        (A) LENGTH: 600 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

Met Phe Phe Ser Arg Gly Ala Leu Ser Leu Ala Val Leu Ser Leu Leu
1               5                   10                  15

Ser Ser Ser Ala Ala Gly Glu Ala Phe Glu Lys Leu Ser Ala Val Pro
            20                  25                  30

Lys Gly Trp His Tyr Ser Ser Thr Pro Lys Gly Asn Thr Glu Val Cys
        35                  40                  45

Leu Lys Ile Ala Leu Ala Gln Lys Asp Ala Ala Gly Phe Glu Lys Thr
    50                  55                  60

Val Leu Glu Met Ser Asp Pro Asp His Pro Ser Tyr Gly Gln His Phe
65                  70                  75                  80

Thr Thr His Asp Glu Met Lys Arg Met Leu Leu Pro Arg Asp Asp Thr
                85                  90                  95

Val Asp Ala Val Arg Gln Trp Leu Glu Asn Gly Gly Val Thr Asp Phe
            100                 105                 110

Thr Gln Asp Ala Asp Trp Ile Asn Phe Cys Thr Thr Val Asp Thr Ala
        115                 120                 125

Asn Lys Leu Leu Asn Ala Gln Phe Lys Trp Tyr Val Ser Asp Val Lys
```

```
            130                 135                 140
His Ile Arg Arg Leu Arg Thr Leu Gln Tyr Asp Val Pro Glu Ser Val
145                 150                 155                 160

Thr Pro His Ile Asn Thr Ile Gln Pro Thr Thr Arg Phe Gly Lys Ile
                165                 170                 175

Ser Pro Lys Lys Ala Val Thr His Ser Lys Pro Ser Gln Leu Asp Val
            180                 185                 190

Thr Ala Leu Ala Ala Val Val Ala Lys Asn Ile Ser His Cys Asp
            195                 200                 205

Ser Ile Ile Thr Pro Thr Cys Leu Lys Glu Leu Tyr Asn Ile Gly Asp
210                 215                 220

Tyr Gln Ala Asp Ala Asn Ser Gly Ser Lys Ile Ala Phe Ala Ser Tyr
225                 230                 235                 240

Leu Glu Glu Tyr Ala Arg Tyr Ala Asp Leu Glu Asn Phe Glu Asn Tyr
                245                 250                 255

Leu Ala Pro Trp Ala Lys Gly Gln Asn Phe Ser Val Thr Thr Phe Asn
                260                 265                 270

Gly Gly Leu Asn Asp Gln Asn Ser Ser Asp Ser Gly Glu Ala Asn
            275                 280                 285

Leu Asp Leu Gln Tyr Ile Leu Gly Val Ser Ala Pro Leu Pro Val Thr
290                 295                 300

Glu Phe Ser Thr Gly Gly Arg Gly Pro Leu Val Pro Asp Leu Thr Gln
305                 310                 315                 320

Pro Asp Pro Asn Ser Asn Ser Asn Glu Pro Tyr Leu Glu Phe Phe Gln
                325                 330                 335

Asn Val Leu Lys Leu Asp Gln Lys Asp Leu Pro Gln Val Ile Ser Thr
                340                 345                 350

Ser Tyr Gly Glu Asn Glu Gln Glu Ile Pro Glu Lys Tyr Ala Arg Thr
            355                 360                 365

Val Cys Asn Leu Ile Ala Gln Leu Gly Ser Arg Gly Val Ser Val Leu
            370                 375                 380

Phe Ser Ser Gly Asp Ser Gly Val Gly Glu Gly Cys Met Thr Asn Asp
385                 390                 395                 400

Gly Thr Asn Arg Thr His Phe Pro Pro Gln Phe Pro Ala Ala Cys Pro
                405                 410                 415

Trp Val Thr Ser Val Gly Ala Thr Phe Lys Thr Thr Pro Glu Arg Gly
            420                 425                 430

Thr Tyr Phe Ser Ser Gly Gly Phe Ser Asp Tyr Trp Pro Arg Pro Glu
            435                 440                 445

Trp Gln Asp Glu Ala Val Ser Ser Tyr Leu Glu Thr Ile Gly Asp Thr
450                 455                 460

Phe Lys Gly Leu Tyr Asn Ser Ser Gly Arg Ala Phe Pro Asp Val Ala
465                 470                 475                 480

Ala Gln Gly Met Asn Phe Ala Val Tyr Asp Lys Gly Thr Leu Gly Glu
            485                 490                 495

Phe Asp Gly Thr Ser Ala Ser Ala Pro Ala Phe Ser Ala Val Ile Ala
            500                 505                 510

Leu Leu Asn Asp Ala Arg Leu Arg Ala Gly Lys Pro Thr Leu Gly Phe
            515                 520                 525

Leu Asn Pro Trp Leu Tyr Lys Thr Gly Arg Gln Gly Leu Gln Asp Ile
            530                 535                 540

Thr Leu Gly Ala Ser Ile Gly Cys Thr Gly Arg Ala Arg Phe Gly Gly
545                 550                 555                 560
```

```
Ala Pro Asp Gly Gly Pro Val Val Pro Tyr Ala Ser Trp Asn Ala Thr
            565                 570                 575

Gln Gly Trp Asp Pro Val Thr Gly Leu Gly Thr Pro Asp Phe Ala Glu
        580                 585                 590

Leu Lys Lys Leu Ala Leu Gly Asn
595                 600
```

(2) INFORMATION FOR SEQ ID NO:3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:3:

TAYAAYATHG GGAYTAYCAR GCYGAYGC                              28

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GCACGCYTGR TTYTGCCAYT CGG                                     23

(2) INFORMATION FOR SEQ ID NO:5:

(i) SEQUENCE CHARACTERISTICS:
        (A) LENGTH: 611 amino acids
        (B) TYPE: amino acid
        (C) STRANDEDNESS: single
        (D) TOPOLOGY: linear (xi) SEQUENCE DESCRIPTION: SEQ ID NO:5:

```
Met Leu Ser Ser Leu Leu Ser Gln Gly Ala Ala Val Ser Leu Ala Val
 1               5                  10                  15

Leu Ser Leu Leu Pro Ser Pro Val Ala Ala Glu Ile Phe Glu Lys Leu
            20                  25                  30

Ser Gly Val Pro Asn Gly Trp Arg Tyr Ala Asn Asn Pro Gln Gly Asn
        35                  40                  45

Glu Val Ile Arg Leu Gln Ile Ala Leu Gln Gln His Asp Val Ala Gly
    50                  55                  60

Phe Glu Gln Ala Val Met Asp Met Ser Thr Pro Gly His Ala Asp Tyr
65                  70                  75                  80

Gly Lys His Phe Arg Thr His Asp Glu Met Lys Arg Met Leu Leu Pro
                85                  90                  95

Ser Glu Thr Ala Val Asp Ser Val Arg Asp Trp Leu Glu Ser Ala Gly
            100                 105                 110

Val His Asn Ile Gln Val Asp Ala Asp Trp Val Lys Phe His Thr Thr
        115                 120                 125

Val Asn Lys Ala Asn Ala Leu Leu Asp Ala Asp Phe Lys Trp Tyr Val
    130                 135                 140

Ser Asp Ala Lys His Ile Arg Arg Leu Arg Thr Leu Gln Tyr Ser Ile
145                 150                 155                 160

Pro Asp Ala Leu Val Ser His Ile Asn Met Ile Gln Pro Thr Thr Arg
                165                 170                 175
```

```
Phe Gly Gln Ile Gln Pro Asn Arg Ala Thr Met Arg Ser Lys Pro Lys
            180                 185                 190
His Ala Asp Glu Thr Phe Leu Thr Ala Ala Thr Leu Ala Gln Asn Thr
        195                 200                 205
Ser His Cys Asp Ser Ile Ile Thr Pro His Cys Leu Lys Gln Leu Tyr
    210                 215                 220
Asn Ile Gly Asp Tyr Gln Ala Asp Pro Lys Ser Gly Ser Lys Ile Gly
225                 230                 235                 240
Phe Ala Ser Tyr Leu Glu Glu Tyr Ala Arg Tyr Ala Asp Leu Glu Arg
                245                 250                 255
Phe Glu Gln His Leu Ala Pro Asn Ala Ile Gly Gln Asn Phe Ser Val
            260                 265                 270
Val Gln Phe Asn Gly Gly Leu Asn Asp Gln Leu Ser Ser Ser Asp Ser
        275                 280                 285
Gly Glu Ala Asn Leu Asp Leu Gln Tyr Ile Leu Gly Val Ser Ala Pro
    290                 295                 300
Val Pro Ile Thr Glu Tyr Ser Thr Gly Gly Arg Gly Glu Leu Val Pro
305                 310                 315                 320
Asp Leu Ser Ser Pro Asp Pro Asn Asp Asn Ser Asn Glu Pro Tyr Leu
                325                 330                 335
Asp Phe Leu Gln Gly Ile Leu Lys Leu Asn Asn Ser Asp Leu Pro Gln
            340                 345                 350
Val Ile Ser Thr Ser Tyr Gly Glu Asp Glu Gln Thr Ile Pro Val Pro
        355                 360                 365
Tyr Ala Arg Thr Val Cys Asn Leu Tyr Ala Gln Leu Gly Ser Arg Gly
    370                 375                 380
Val Ser Val Ile Phe Ser Ser Gly Asp Ser Gly Val Gly Ala Ala Cys
385                 390                 395                 400
Leu Thr Asn Asp Gly Thr Asn Arg Thr His Phe Pro Pro Gln Phe Pro
                405                 410                 415
Ala Ser Cys Pro Trp Val Thr Ser Val Gly Ala Thr Ser Lys Thr Ser
            420                 425                 430
Pro Glu Gln Ala Val Ser Phe Ser Ser Gly Gly Phe Ser Asp Leu Trp
        435                 440                 445
Pro Arg Pro Ser Tyr Gln His Ala Ala Val Gln Thr Tyr Leu Thr Lys
    450                 455                 460
His Leu Gly Asn Lys Phe Ser Gly Leu Phe Asn Ala Ser Gly Arg Ala
465                 470                 475                 480
Phe Pro Asp Val Ser Ala Gln Gly Val Asn Tyr Ala Val Tyr Asp Lys
                485                 490                 495
Gly Met Leu Gly Gln Phe Asp Gly Thr Ser Cys Ser Ala Pro Thr Phe
            500                 505                 510
Ser Gly Val Ile Ala Leu Leu Asn Asp Ala Arg Leu Arg Ala Gly Leu
        515                 520                 525
Pro Val Met Gly Phe Leu Asn Pro Phe Leu Tyr Gly Val Gly Ser Glu
    530                 535                 540
Lys Gly Ala Leu Asn Asp Ile Val Asn Gly Gly Ser Val Gly Cys Asp
545                 550                 555                 560
Gly Arg Asn Arg Phe Gly Gly Thr Pro Asn Gly Ser Pro Val Val Pro
                565                 570                 575
Phe Ala Ser Trp Asn Ala Thr Thr Gly Trp Asp Pro Val Ser Gly Leu
            580                 585                 590
Gly Thr Pro Asp Phe Ala Lys Leu Lys Gly Val Ala Leu Gly Glu Glu
```

```
                595                    600                    605

Gly Gly Asn
        610

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:6:

GGGATTTAAA TATGTTCTTC AGTCGT                                          26

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GGGTTAATTA ATTAGTTGCC AAGGGC                                          26
```